(12) United States Patent
Seppi

(10) Patent No.: US 7,672,426 B2
(45) Date of Patent: Mar. 2, 2010

(54) RADIATION SCANNING UNITS WITH REDUCED DETECTOR REQUIREMENTS

(75) Inventor: Edward J. Seppi, Portola Valley, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 545 days.

(21) Appl. No.: 11/149,733

(22) Filed: Jun. 10, 2005

(65) Prior Publication Data

US 2006/0023835 A1   Feb. 2, 2006

Related U.S. Application Data

(63) Continuation-in-part of application No. 10/310,060, filed on Dec. 4, 2002.

(51) Int. Cl.
*G01N 23/04*   (2006.01)
(52) U.S. Cl. .......................... 378/57; 378/20
(58) Field of Classification Search ............... 378/4–20, 378/57
See application file for complete search history.

(56) References Cited

U.S. PATENT DOCUMENTS

| | | | |
|---|---|---|---|
| 3,158,744 A | 11/1964 | Bernstein | |
| 3,636,353 A | 1/1972 | Untermyer | |
| RE28,544 E | 9/1975 | Stein et al. | |
| 3,924,132 A | 12/1975 | Koslow | |
| 4,031,545 A | 6/1977 | Stein et al. | |
| 4,149,081 A | 4/1979 | Seppi | |
| 4,196,352 A | 4/1980 | Berninger et al. | |
| 4,229,654 A | 10/1980 | Arya | |
| 4,251,726 A | 2/1981 | Alvarez | |
| 4,352,021 A | 9/1982 | Boyd et al. | |
| 4,357,535 A | 11/1982 | Haas | |
| 4,382,208 A | 5/1983 | Meddaugh et al. | |
| 4,400,650 A | 8/1983 | Giebeler, Jr. | |
| 4,422,177 A | 12/1983 | Mastronardi et al. | |
| 4,430,568 A | 2/1984 | Yoshida et al. | |
| 4,521,900 A | 6/1985 | Rand | |
| 4,599,740 A | 7/1986 | Cable | |
| 4,600,998 A | 7/1986 | Huet | |

(Continued)

FOREIGN PATENT DOCUMENTS

WO   WO-96/13839   5/1996

(Continued)

OTHER PUBLICATIONS

McDonald, Marci, "Checkpoint Terror Border Searches Snarl the Free Flow of Goods", U.S. News and World Report, Feb. 11, 2002, p. 52.

(Continued)

*Primary Examiner*—Hoon Song
(74) *Attorney, Agent, or Firm*—Kaye Scholer LLP; Brandon N. Sklar, Esq.

(57) ABSTRACT

In one embodiment, a scanning unit for inspecting cargo conveyances uses a partial radiation beam and a detector of reduced length. In another embodiment, a scanning unit for inspecting objects comprises a detector with gaps along its expanse. In both cases, the cost of the scanning system may be reduced. The object, the source, and or the detector may be moved to enable generation of computed tomographic images. Methods are disclosed, as well.

40 Claims, 14 Drawing Sheets

U.S. PATENT DOCUMENTS

| | | | |
|---|---|---|---|
| 4,631,741 A | 12/1986 | Rand et al. | |
| 4,671,256 A | 6/1987 | Lemelson | |
| 4,722,096 A | 1/1988 | Dietrich et al. | |
| 4,769,830 A | 9/1988 | Peterson et al. | |
| 4,824,349 A | 4/1989 | Oku et al. | |
| 4,839,913 A | 6/1989 | Annis et al. | |
| 4,918,315 A | 4/1990 | Gomberg et al. | |
| 4,941,162 A | 7/1990 | Vartsky et al. | |
| 4,956,856 A | 9/1990 | Harding | |
| 4,963,746 A | 10/1990 | Morgan et al. | |
| 4,987,584 A | 1/1991 | Doenges | |
| 5,044,002 A | 8/1991 | Stein | |
| 5,065,418 A | 11/1991 | Bermbach et al. | |
| 5,076,993 A | 12/1991 | Sawa et al. | |
| 5,098,640 A | 3/1992 | Gozani et al. | |
| 5,115,459 A | 5/1992 | Bertozzi | |
| 5,117,445 A | 5/1992 | Seppi et al. | |
| 5,124,554 A | 6/1992 | Fowler et al. | |
| 5,153,439 A | 10/1992 | Gozani et al. | |
| 5,175,756 A | 12/1992 | Pongratz et al. | |
| 5,200,626 A | 4/1993 | Schultz et al. | |
| 5,278,418 A | 1/1994 | Broadhurst | |
| 5,313,511 A | 5/1994 | Annis et al. | |
| 5,323,004 A | 6/1994 | Ettinger et al. | |
| 5,367,552 A | 11/1994 | Peschmann | |
| 5,410,156 A | 4/1995 | Miller | |
| 5,420,905 A | 5/1995 | Bertozzi | |
| 5,442,672 A | 8/1995 | Bjorkholm et al. | |
| 5,467,377 A * | 11/1995 | Dawson | 378/19 |
| 5,490,218 A | 2/1996 | Krug et al. | |
| 5,491,734 A | 2/1996 | Boyd et al. | |
| 5,493,596 A | 2/1996 | Annis | |
| 5,495,106 A | 2/1996 | Mastny | |
| 5,524,133 A | 6/1996 | Neale et al. | |
| 5,557,108 A | 9/1996 | Tumer | |
| 5,567,552 A | 10/1996 | Ham | |
| 5,600,303 A | 2/1997 | Husseiny et al. | |
| 5,600,700 A | 2/1997 | Krug et al. | |
| 5,611,502 A | 3/1997 | Edlin et al. | |
| 5,638,420 A | 6/1997 | Armistead | |
| 5,642,394 A | 6/1997 | Rothschild | |
| 5,648,996 A | 7/1997 | Gupta | |
| 5,692,028 A | 11/1997 | Geus et al. | |
| 5,692,029 A | 11/1997 | Husseiny et al. | |
| 5,692,507 A | 12/1997 | Seppi et al. | |
| 5,696,806 A | 12/1997 | Grodzins et al. | |
| 5,729,582 A | 3/1998 | Ham et al. | |
| 5,784,430 A | 7/1998 | Sredniawski | |
| 5,818,054 A | 10/1998 | Randers-Pehrson et al. | |
| 5,838,758 A | 11/1998 | Krug et al. | |
| 5,838,759 A | 11/1998 | Armistead | |
| 5,841,832 A | 11/1998 | Mazess et al. | |
| 5,917,880 A | 6/1999 | Bjorkholm | |
| 5,917,883 A | 6/1999 | Khutoryansky et al. | |
| 5,930,326 A | 7/1999 | Rothschild et al. | |
| 5,963,614 A * | 10/1999 | Hu et al. | 378/15 |
| 5,966,422 A | 10/1999 | Dafni et al. | |
| 5,970,115 A | 10/1999 | Colbeth et al. | |
| 5,974,111 A | 10/1999 | Krug et al. | |
| 6,018,562 A | 1/2000 | Willson | |
| 6,041,097 A | 3/2000 | Roos et al. | |
| 6,078,642 A | 6/2000 | Simanovsky et al. | |
| 6,088,423 A | 7/2000 | Krug et al. | |
| 6,148,058 A | 11/2000 | Dobbs | |
| 6,151,381 A | 11/2000 | Grodzins et al. | |
| 6,198,790 B1 | 3/2001 | Pflaum | |
| 6,218,943 B1 | 4/2001 | Ellenbogen | |
| 6,236,709 B1 | 5/2001 | Perry et al. | |
| 6,249,567 B1 | 6/2001 | Rothschild et al. | |
| 6,259,762 B1 | 7/2001 | Pastyr et al. | |
| 6,269,142 B1 | 7/2001 | Smith | |
| 6,278,115 B1 | 8/2001 | Annis et al. | |
| 6,292,533 B1 | 9/2001 | Swift et al. | |
| 6,295,331 B1 * | 9/2001 | Hsieh | 378/19 |
| 6,347,132 B1 | 2/2002 | Annis | |
| 6,358,377 B1 | 3/2002 | Schloremberg et al. | |
| 6,366,021 B1 | 4/2002 | Meddaugh et al. | |
| 6,408,088 B1 | 6/2002 | Hu | |
| 6,411,674 B1 | 6/2002 | Oikawa | |
| 6,438,201 B1 | 8/2002 | Mazess et al. | |
| 6,490,337 B1 | 12/2002 | Nagaoka et al. | |
| 6,512,809 B2 * | 1/2003 | Doubrava et al. | 378/19 |
| 6,567,496 B1 | 5/2003 | Sychev | |
| 6,584,170 B2 | 6/2003 | Aust et al. | |
| 6,619,839 B2 | 9/2003 | Yoshimura | |
| 6,628,745 B1 | 9/2003 | Annis et al. | |
| 6,661,865 B1 | 12/2003 | Popilock | |
| 6,687,328 B2 | 2/2004 | Bavendiek et al. | |
| 6,735,274 B1 | 5/2004 | Zahavi et al. | |
| 6,785,360 B1 | 8/2004 | Annis | |
| 6,800,858 B1 | 10/2004 | Seppi | |
| 6,848,808 B2 | 2/2005 | Guerrieri | |
| 6,965,661 B2 | 11/2005 | Kojima et al. | |
| 7,062,011 B1 * | 6/2006 | Tybinkowski et al. | 378/57 |
| 7,356,115 B2 | 4/2008 | Ford et al. | |
| 2002/0037068 A1 | 3/2002 | Oikawa | |
| 2004/0109532 A1 | 6/2004 | Ford et al. | |

FOREIGN PATENT DOCUMENTS

WO    WO 2004/051311 A2    6/2004

OTHER PUBLICATIONS

Revkin, Andrew C., "Possibility of Using Trucks for Terror Remains Concern", NYTimes.com, Oct. 20, 2002, pp. 1-5, The New York Times Company, New York City, NY.

Grodzins, Lee, "Nuclear Techniques for Finding Chemical Explosives in Airport Luggage; Beam Interactions with Materials and Atoms", May 1991, pp. 829-833, vol. B56/57, Part II.

Avinash C. Kak and Malcolm Slaney; "Principles of Computerized Tomographic Imaging"; IEEE Press, 1988; Chapter 3 entitled Algorithms for Reconstruction with Nondiffracting Sources, pp. 49-112; Available at http://www.slaney.org/pct/pct-toc.html.

* cited by examiner

RADIATION SCANNING UNITS WITH REDUCED DETECTOR REQUIREMENTS

RELATED APPLICATION

The present application is a continuation-in-part of application Ser. No. 10/310,060, which was filed on Dec. 4, 2002, is assigned to the assignee of the present invention, and is incorporated by reference, herein.

FIELD OF THE INVENTION

Radiation scanning of objects and, more particularly, radiation scanning of objects to reconstruct computed tomographic images.

BACKGROUND OF THE INVENTION

Radiation is commonly used in the non-invasive inspection of objects such as luggage, bags, briefcases and the like, to identify hidden contraband at airports and public buildings. The contraband may include hidden guns, knives, explosive devices and illegal drugs, for example.

To obtain additional information about the contents of the luggage and other objects, detectors may be provided to detect scattered radiation, as described in U.S. Pat. No. 5,642, 394, for example. Systems may combine detection of scattered radiation with the detection of transmitted radiation.

Another technique to enhance the information that may be derived about the composition of the contents of an object is to scan the object with radiation beams having two different energy distributions. A ratio of the attenuation detected at two energy levels is indicative of the atomic numbers of the material through which the radiation beam passes. Dual energy systems enable better detection of plastic materials and illegal drugs, for example.

One disadvantage of radiographic imaging is that all items within the object in the path of the radiation beam are superimposed on the image. If there are many items in the object, it may be difficult to distinguish among them. The identification of dangerous items is thereby hampered. In addition, the orientation and shape of the items within the object could affect whether they can be identified on a radiograph. Thin sheets of explosive materials may also be difficult to identify on a radiograph, particularly if they are oriented perpendicular to the scanning beam.

Computed tomography ("CT") enables the reconstruction of the cross-sectional images of the contents of an object, facilitating the identification of the items in the luggage. CT images also provide higher resolution, greater image contrast and greater sensitivity to characteristics of the object being scanned, than radiographs. However, reconstruction of CT images of an object requires a large number of scans of the object at a plurality of angles. Conducting a sufficient number of scans for CT reconstruction is time consuming. Depending on the system used, CT imaging of an entire piece of luggage may be too slow for practical use in screening luggage in airports, for example.

In U.S. Pat. No. 5,567,552 ("the '552 patent"), a source of X-ray radiation is provided on one side of an inner surface of a rotating module and a detector array is provided on the opposite side. Luggage is moved through the module incrementally. The module rotates to scan the luggage at a plurality of angles, at each incremental position. The inspection speed may be increased by pre-screening with a line-scan. Then, only suspicious regions identified by the prescreening step are subjected to CT imaging. U.S. Pat. No. 6,078,642 ("the '642 patent") discloses a CT scanning system for luggage similar to the '552 patent, where data processing techniques are used to speed the inspection rate to scan the entire piece of luggage, without requiring pre-scanning. The module rotates as a piece of luggage is continuously moved through the module, providing helical volumetric CT scanning.

U.S. Pat. No. 5,410,156 discloses an explosives detection system for scanning luggage in airports including a neutron radiation source on one side of an object and a two dimensional detector array on the opposite side of the object. The object is supported on a rotatable platform. Rotation of the platform during scanning enables optional tomographic imaging of an object on the platform, to create three dimensional distributions of hydrogen, carbon, nitrogen and oxygen per a cubic volume through the sample. The ratios of these elements are determined for small volume increments of the sample. Neural net methods are used to determine whether a volume increment contains an explosive.

While the smuggling of contraband, such as guns and explosives, onto planes in carry-on bags and in luggage has been a well known, ongoing concern, a less publicized but also serious threat is the smuggling of contraband across borders and by boat in large cargo containers. Only a small proportion of the cargo containers brought to the United States by boat are inspected, for example. "Checkpoint terror", U.S. News and World Report, Feb. 11, 2002, p. 52.

Standard cargo containers are typically 20-50 feet long (6.1-15.2 meters), 8 feet high (2.4 meters) and 6-9 feet wide (1.8-2.7 meters). Air cargo containers, which are used to contain a plurality of pieces of luggage or other cargo to be stored in the body of an airplane, may range in size (length, height, width) from about 35×21×21 inches (0.89×0.53×0.53 meters) up to about 240×118×96 inches (6.1×3.0×2.4 meters). Large collections of objects, such as many pieces of luggage, may also be supported on a pallet. Pallets, which may have supporting sidewalls, may be of comparable sizes as cargo containers, at least when supporting objects. The term "cargo conveyance" is used to refer to all types of cargo containers and comparably sized pallets (and other such platforms) supporting objects.

In contrast to the size ranges of cargo conveyances, typical airport scanning systems for carry-on bags have tunnel entrances up to about 0.40×0.60 meters. Scanning systems for checked luggage have travel openings that are only slightly larger. Since only bags that fit through the tunnel may be inspected, such systems cannot be used to inspect cargo containers. The low energies used in typical X-ray luggage and bag scanners, described above, are also too low to penetrate through the much larger cargo containers. In addition, many such systems are too slow to economically inspect larger objects, such as cargo containers.

It is known to inspect cargo containers supported by vehicles, such as trucks, by mobile systems. For example, in U.S. Pat. No. 5,638,420, large containers are inspected by a system on a movable frame. A source of a fan beam, a cone beam or a pencil beam of X-ray radiation, such as a linear accelerator with an accelerating potential in the MeV range, is mounted on one side of the frame. A detector array is mounted on an opposing side of the frame. The frame may be self-propelled and advances across the length of the container. Radiographic images are generated for analysis by an operator. Other mobile systems are disclosed in U.S. Pat. Nos. 6,292,553 and 5,917,883, for example.

The high resolution, improved image contrast and the ability to distinguish small differences in characteristics of items within an object that are provided by CT scanning would be advantageous in the inspection of cargo conveyances. The CT scanning units used in airports for luggage and the like discussed above are not readily scaleable to the large sizes required to scan cargo containers. For example, to accommodate most cargo conveyances, the rotating modules of the '552 patent or the '642 patent would need to be greatly enlarged. Such large rotating units, carrying both the sources and the detectors, would be very expensive and would be difficult to operate and maintain.

U.S. Pat. No. 6,628,745 B1 discloses a CT system for cargo containers comprising a rotating and vertically displaceable platform to support the container. An electron beam is magnetically deflected along a linear target, as the container is rotated, to generate a radiation beam that moves along the target to scan a slice of the container. CT images may be generated from the detected radiation. An elevator then moves the platform vertically and the container is scanned again to form CT images of other slices.

FIG. 1 is a front view of an example of a detector module 1 known in the art. In this example, the detector module 1 comprises a housing 2, a detector element section 3 within the housing and an electronics section within the housing. The housing 2 defines an open window in front of the detector element section 3 for radiation to pass through. Behind the window are detector elements 4. The electronics sections 5, 6, 7 comprise digital drivers in sections 5, 6 and analog readouts in section 7. In some detector modules, the digital drivers may only be provided on one side of the module, in section 5, for example. In use, shielding material (not shown) is placed in front of the electronics sections 5, 6, 7 to protect the electronics from damage by radiation. However, the shielding in front of the electronics sections 5, 6, 7 may not be sufficient to protect the electronics at the high levels of radiation, such as at 6 MeV and above, necessary to penetrate through larger cargo conveyances.

Despite the various designs for the inspection of large objects such as cargo containers disclosed in the patents discussed above and in other references, much of the inspection of cargo conveyances is done manually, if at all. "Checkpoint terror", U.S. News and World Report, Feb. 11, 2002, p. 52. Practical, efficient, non-intrusive CT radiation scanners for the inspection of large objects, such as cargo conveyances, are still needed. Improved radiation scanners for the inspection of smaller objects, such as luggage, including improved CT imaging of smaller objects, are also needed.

SUMMARY OF THE INVENTION

Cost may be one factor precluding the use of CT imaging of cargo conveyances and luggage. Detectors, which are expensive components of a CT scanning system, contribute to the high cost of the system. Deterioration of detector electronics due to exposure to the high radiation energies required to penetrate cargo conveyances, despite shielding, contributes to the maintenance costs of the system.

In accordance with one embodiment, a scanning unit for inspecting cargo conveyances is disclosed comprising a radiation source to emit a beam of radiation and a rotatable platform adapted to support a cargo conveyance for inspection by the beam of radiation. The rotatable platform is rotatable about an axis. A detector is positioned to collect at least certain of the radiation transmitted through the cargo conveyance. At least one of the platform, the source, and the detector is movable along a direction of the axis. The detector is configured to collect a sufficient data set of radiation to reconstruct computed tomographic images. At least some line integrals through the cargo conveyance are measured only once. A processor may be coupled to the detector to reconstruct computed tomography images from data received from the detector. The source and the detector may be stationary and the platform may be movable along the axis, for example.

In one related embodiment, the source is configured to emit a beam of radiation having a first boundary extending beyond an edge of the cargo conveyance and a second boundary intercepting the cargo conveyance during rotation of the object, during scanning. The detector has a reduced length as compared to a system where both boundaries of the radiation beam extend beyond the boundary of the cargo conveyance.

In another related embodiment, the detector may have an expanse and at least one gap across the expanse. The gap may be defined by a separation between at least two adjacent detector modules in a detector array. The at least one gap may comprise a plurality of gaps and the modules may be positioned with respect to a ray from the source through an axis of rotation of the platform during rotation by the platform such that a mirror image of first detector modules on one side of the ray, projected onto the other side of the ray, at least coincides with the gaps between second detector modules on the other side of the ray. The projection of the mirror image of the first detector modules preferably coincides with the gaps and overlaps portions of the second modules. The processor may be configured to apply at least one first weighting value to data collected by overlapping portions of the detector modules and apply at least one second weighting value to data collected from detector elements in non-overlapping portions of the detector modules. The first weighting value is less than the second weighting value.

In accordance with another embodiment of the invention, a scanning unit for inspecting objects is disclosed comprising a radiation source to emit a beam of radiation and a rotatable platform to support an object for inspection by the beam of radiation. The rotatable platform is rotatable about an axis. At least one of the radiation source, the platform and the detector is movable along a direction of the axis. The source and the detector may be stationary and the platform may be movable along the axis, for example.

A detector array is positioned to receive radiation transmitted through the object, comprising a first plurality of modules separated by a second plurality of gaps. The plurality of modules are positioned with respect to a ray from the source through a center of rotation of the object during rotation by the platform such that a mirror image of first detector modules on one side of the ray, projected onto the other side of the ray, at least coincides with the gaps between second detector modules on the other side of the array. Preferably, in the projection, the first detector modules coincide with the gaps and overlap portions of the first detector modules.

The radiation beam may be a fan beam or a cone beam, for example. If the beam is a cone beam, the detector array comprises a plurality of rows and columns of detector modules separated by respective first gaps between detector modules in adjacent rows and by respective second gaps between detector modules in adjacent columns. The rows of detector modules are positioned so that a first projection of the detector modules on one side of a first axis perpendicular to the first ray and perpendicular to a direction of the rows, onto the other side of the first axis, at least coincides with the plurality of gaps on the other side. The columns are positioned so that a projection of the detector modules on one side of a second axis perpendicular to the first ray and perpendicular to a direction of the columns onto the other side of the axis at least coincides with the plurality of gaps on the other side.

A processor may be programmed to reconstruct computed tomography images based, at least in part, on radiation collected by the detector array. If the projection of the mirror image of the first detector modules coincides with the gaps and overlaps portions of the second modules, the processor may be configured to apply at least one first weighting value to data collected by overlapping portions of the detector modules and at least one second weighting value to data collected from detector elements in non-overlapping portions of the detector modules. The first weighting value is less than the second weighting value.

In accordance with another embodiment, a radiation scanning system comprises a radiation source and a detector comprising an expanse of detector modules and defining at least one gap between adjacent detector modules along the expanse. A movable platform is provided to support the object. A processor is provided to reconstruct computed tomographic images based, at least in part, on data provided by the detector. The at least one gap is positioned such that at least some line integrals through the object are measured only once. The at least one gap may be positioned such that a mirror image of the expanse of first detector modules on one side of a ray from the source through the object, projected onto the other side of the ray, at least coincides with the at least one gap between second detector modules on the other side of the ray.

In the projection, the first detector modules may overlap respective portions of the second detector modules. The processor may then be configured to apply at least one first weighting value to data collected by overlapping portions of the detector modules and apply at least one second weighting value to data collected from detector elements in non-overlapping portions of the detector modules, wherein the first weighting value is less than the second weighting value.

The radiation source may be movable around the object and the detector array may be movable with movement of the source. In this case, the detector array may extend only partially around the object. Alternatively, the radiation source may be movable around the object and the detector array is stationary. In this case, detector array may extend completely around the object.

In accordance with another embodiment, a method of examining contents of a cargo conveyance is disclosed comprising rotating the cargo conveyance about an axis of rotation and scanning the cargo conveyance with a radiation beam. The method further comprises measuring at least some line integrals though the cargo conveyance only once and reconstructing computed tomographic images based on the detected radiation.

In accordance with another embodiment of the invention, a method of examining contents of an object is disclosed comprising scanning the object with a radiation beam, detecting radiation in at least one first location on one side of the ray passing through the object and not in at least one second other location, and detecting radiation in at least one third location on the other side of a ray and not in at least one fourth location. In a projection of a mirror image of the one side of the ray onto the other side of the ray, the at least one first location on the one side at least coincides with the at least one fourth location on the other side. The radiation may be detected by a first plurality of detector modules separated by a second plurality of gaps. The source may be moved around the object while scanning. Radiation may be detected by a stationary detector array extending around the object or by a detector array that moves with movement of the source.

As used herein, the term "at least one of" means any one or more of the following.

DESCRIPTION OF PREFERRED EMBODIMENTS

In an embodiment of the present invention, the length of a detector array is reduced by using a partial radiation beam to scan the object. In another embodiment, the number of detector modules in a detector array is reduced by providing gaps along the length of the detector array and compensating for the lack of data collected in the gaps.

Figure 2:
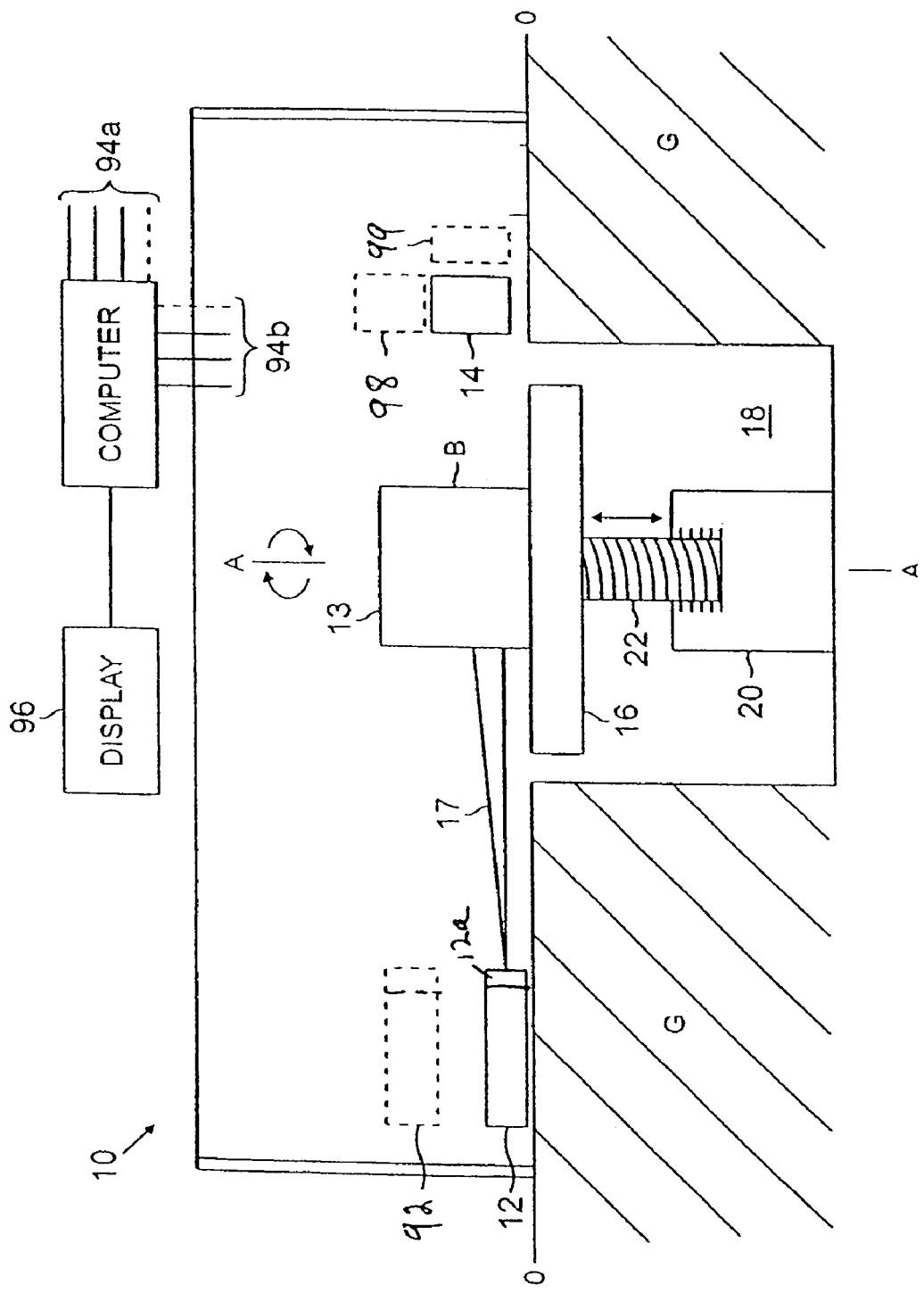
FIG. 2 is a side view of a scanning unit according to one embodiment of the invention, showing a rotatable, vertically displaceable platform in an initial position.

FIG. 2 is a side view of an example of a scanning unit 10 that may be configured to implement embodiments of the present invention. In this example, the scanning unit 10 comprises a source of radiation 12, such as a source of X-ray radiation, to irradiate an object 13 being scanned, a detector 14 to detect radiation transmitted through the object 13 and a rotating/vertically displaceable platform 16 to support and position the object during scanning. The rotating/vertically displaceable platform 16 is between the source 12 and the detector 14. A collimator 12a collimates the generated radiation into a horizontally diverging beam 17 of radiation. The detector 14 may extend horizontally to detect the beam 17 after transmission through the object 13. The horizontally diverging beam may be a cone beam that also diverges vertically, as shown in FIG. 2, or a fan beam, for example. The object 13 may be a large object, such as a cargo conveyance (cargo container and pallets, for example). The object 13 may also be a smaller object, such as a piece of luggage or a carry-on bag, for example. Shielding 90 is provided around the scanning unit 10, as is known in the art and is described in application Ser. No. 10/316,060 (the '060 Application), which was filed on Dec. 4, 2002, is assigned to the assignee of the present invention, and is incorporated by reference, herein.

The source 12 and the detector 14 are preferably stationary and the platform 16 is preferably movable vertically. It is advantageous to use a stationary source and a stationary detector because the characteristics of those devices may be optimized without being concerned or as concerned about the weight and size of a moving source and/or detector, particularly when the source and/or detector need to be moved around a large object, such as a cargo conveyance. While preferred, it is not required that the source 12 and the detector 14 be stationary. Examples of movable sources and detectors are described in other examples, below.

Figure 3:
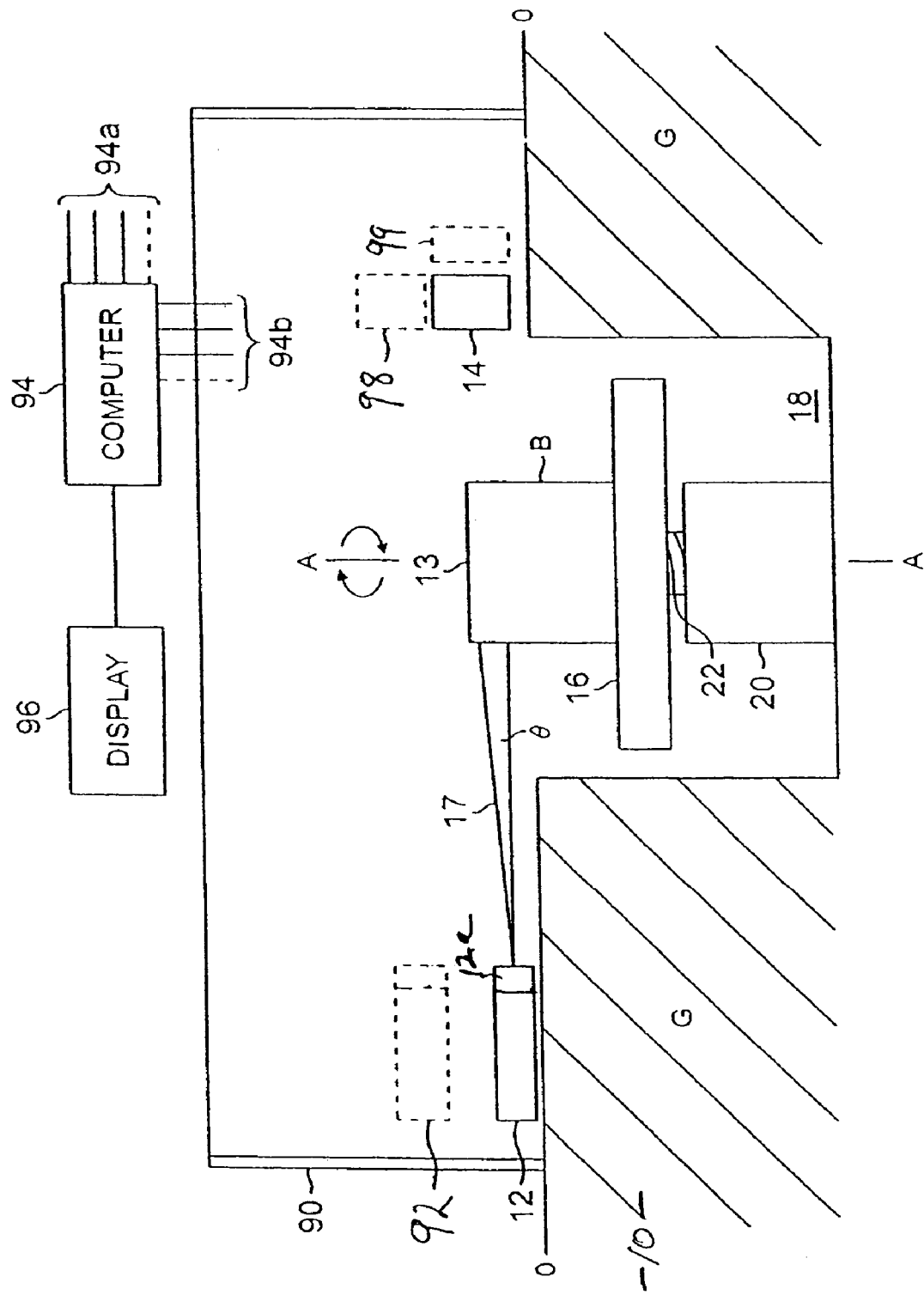
FIG. 3 is a side view of the scanning unit of FIG. 2, wherein the platform is shown in a raised position.

In FIG. 2, the source 12 and the detector 14 are supported at ground level 0. The platform 16 is in an initial position, also at ground level 0. The object 13 is secured to the platform 16, as discussed below. A drive system 20 is coupled to the platform 16. The drive system 20 is within a cavity 18, which may be in the ground G. The cavity 18 may be in the ground G. In this example, the drive system 20 moves the platform up and down in the cavity 18. FIG. 3 is a side view of the scanning unit 10 of FIG. 2, where the platform 16 is lowered into the cavity 18. A conveying system, discussed with respect to FIG. 4, below, moves the object 13 to the platform 16 along an axis perpendicular to the page.

The platform 16 may be a flat plate. In this example, the platform 16 the drive system 20 both rotates the platform about a vertical axis "A" through a center of the plate and moves the platform 16 vertically along the axis. The direction of rotation may be clockwise or counter clockwise when moving vertically in both directions. The direction of rotation may also be clockwise when moving vertically in one direction and counter clockwise when moving vertically in the opposite direction. The drive system 20 may be one in which the vertical travel of the platform 16, and hence the vertical travel of the object 13 supported by the plate, is a function of the rotation of the platform 16, but that is not required. The speed of movement of the platform 16 is preferably such that the object 13 is stationary with respect to the platform and the contents of the object are stationary with respect to the object as the object is moved. A suitable rate of rotation and vertical movement of the platform 16 may be readily determined by one of skill in the art of radiation and computed tomographic imaging, taking into consideration the packing of the contents of the object 13. All or a portion of the platform 16, and any other components of the scanning unit 10, may be made of material transparent to X-ray or other radiation, if necessary.

The drive system 20 may comprise a screw jack, for example, comprising a threaded post 22 supporting the platform 16, as shown in FIG. 2. The threaded post 22 is received within a threaded cavity of a motor box. Rotation of the post 22 by a motor (not shown) causes rotation of the post. In a basic screw jack, rotation in one direction raises the platform and rotation in the opposite direction lowers the platform. The screw jack could also have a double helical groove that switches the direction of the pitch. A ball bearing trapped within the helical groove and a race on the platform 16 oscillates the platform up and down continuously or incrementally as the platform is rotated in one direction, as is known in the art. Examples of electromechanical, hydraulic, and pneumatic driving systems are described in the '060 Application, which is incorporated by reference herein. Other electromechanical, hydraulic and/or pneumatic driving mechanisms may also be used.

Figure 4:
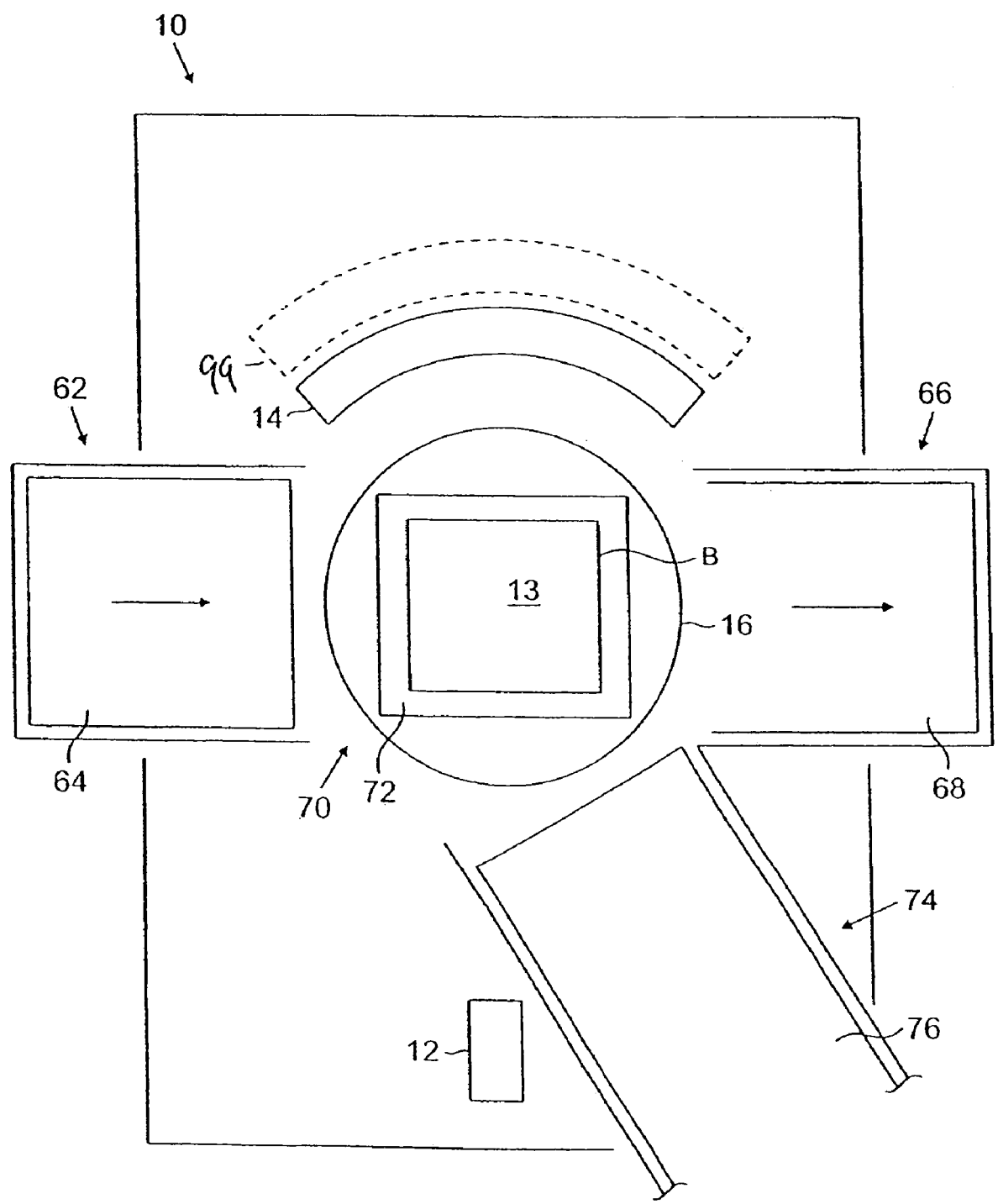
FIG. 4 is a top view of the interior of the scanning unit of the embodiment of FIG. 1.

FIG. 4 is a top view of the interior of the scanning unit 10 of the example of FIG. 2. Here, the platform 16 is circular and is larger than the object 13. The platform 16 may be other shapes and sizes, as well. A conveyor system may be provided to convey the object 13 to and from the platform 16. In this example, the conveyor system comprises a first portion 62 comprising a first conveyor belt 64 that extends from the outside of the scanning unit 10 to the platform 16. A second portion 66 comprises a second conveyor belt 68 extending from the platform 16 to the exterior of the scanning unit 10, providing an exit path for the object 13. A third portion 70 of the conveying system may be provided, comprising a third belt 72 on the platform 16, to convey the object 13 from the first belt and to properly position the object 13 on the platform 16. The third belt 72 also conveys the object 13 to the second belt 68 after scanning is completed. The conveying system may optionally include a fourth portion 74 comprising a fourth conveyor belt 76 to convey suspicious objects along a second exit path from the platform 16, for further inspection. A suspicious object 13 may be directed to the fourth portion 74 by rotating the platform 16. Suspicious objects may be steered along the fourth portion and returned to the platform 16 for additional scanning when there is time, as described in the '060 Application, which is incorporated by reference herein.

In addition, the configuration of the conveyor system may be varied such that the source, detector, entrance and exit are at different levels, as is also described and illustrated in the '060 Application, which is incorporated by reference herein. Instead of providing one or two exit paths and associated conveyor belts, the first conveyor belt 64 may be used to both convey the object 13 to the platform 16 and to convey the object 13 from the platform 16. Other devices for conveying objects, such as rotating rollers, may be used instead of conveying belts.

Figure 7:
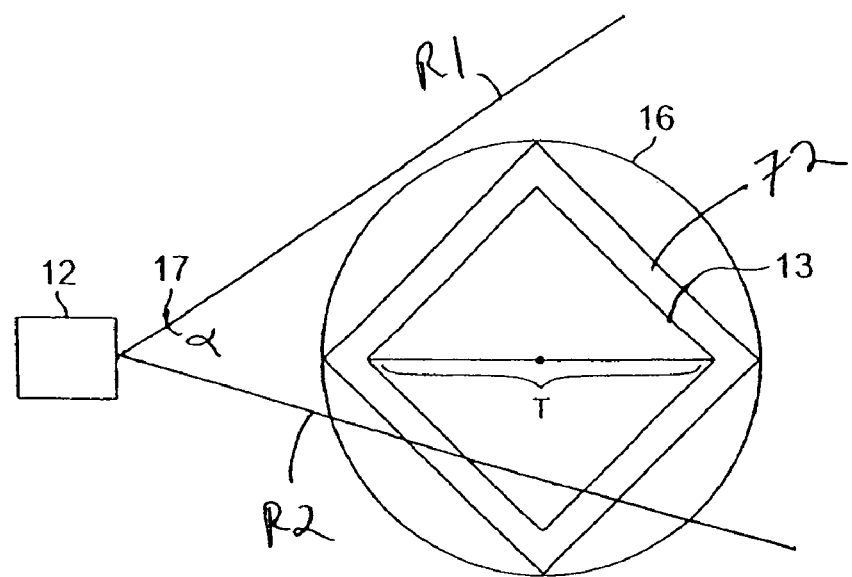
FIG. 7 is a top view of an object on the platform, where the longest thickness of the object during rotation is shown aligned with the radiation beam.

The X-ray source 12 may be a source of Bremsstrahlung radiation, for example. The source 12 should generate X-ray radiation with high enough energy to penetrate through the thickness of the object 13 while the object is in any rotational orientation on the platform 16. For example, for X-ray radiation to penetrate through a rectangular cargo conveyance, such as a cargo container or other rectangular object 13 whose largest thickness "T" along the radiation beam 17 during rotation is greater than about 5 feet (1.5 meters), radiation beams with average or median energies over 1 MeV may be used. In a rectangular object 13, the largest thickness T is between opposing corners of the object, as shown in FIG. 7.

Figure 5:
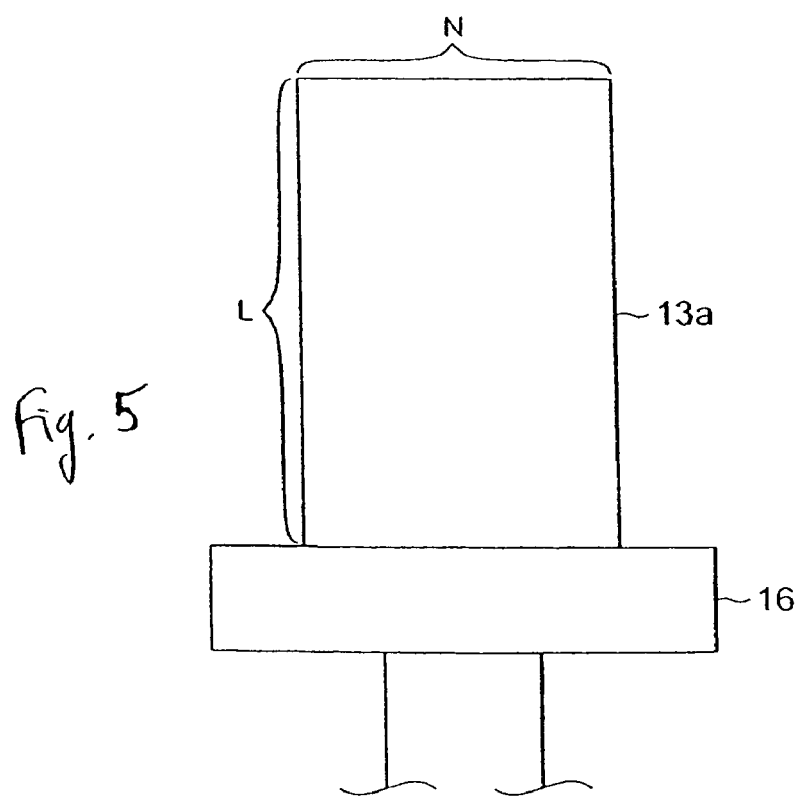
FIG. 5 is a side view of a long object, such as a standard cargo container, on the platform.

To scan long objects, such as a standard cargo container 13a, which is about 20 feet long (about 6.1 meters) and about 6-9 feet wide (1.8-2.7 meters), the container may be placed in an upright position on the platform 16, as shown in FIG. 5. The radiation beam would then intercept a diameter through the width "N" of the object, which is not as thick as the length "L" of the object. As mentioned above, a radiation beam having an average or median energy greater than 1 MeV may be used to scan a standard cargo container 13a oriented on the platform 16 as shown in FIG. 5. The radiation beam may have an average or median energy of about 3 MeV or more, for example. It is noted that depending on the packing and other characteristics of the contents of the cargo container, it might not be practical to place all standard cargo containers in an upright position. It is also noted that X-ray radiation in the kilovoltage range may be used to penetrate through smaller cargo containers and other smaller objects.

If X-ray radiation greater than about 1 MeV is needed to penetrate through the object 13, the X-ray source 12 may be a linear accelerator, such as a Linatron® Linear Accelerator ("Linatron°"), having an accelerating potential in a range of about 2 MeV or more, available from Varian Medical Systems, Inc., Palo Alto, Calif. ("Varian"), for example. The source may or may not be pulsed. In the Varian Linatron®, 360 pulses are output per second, for example. Other high energy X-ray sources may be used as well, such as electrostatic accelerators, microtrons and betatrons, for example. The X-ray source may also be a radioisotope, such as Cobalt-60, which emits nearly monoenergetic radiation beams. Other sources of monoenergetic radiation may be used, as well. If lower energy X-ray radiation may be used, the source 12 may be an X-ray tube, for example.

Figure 6:
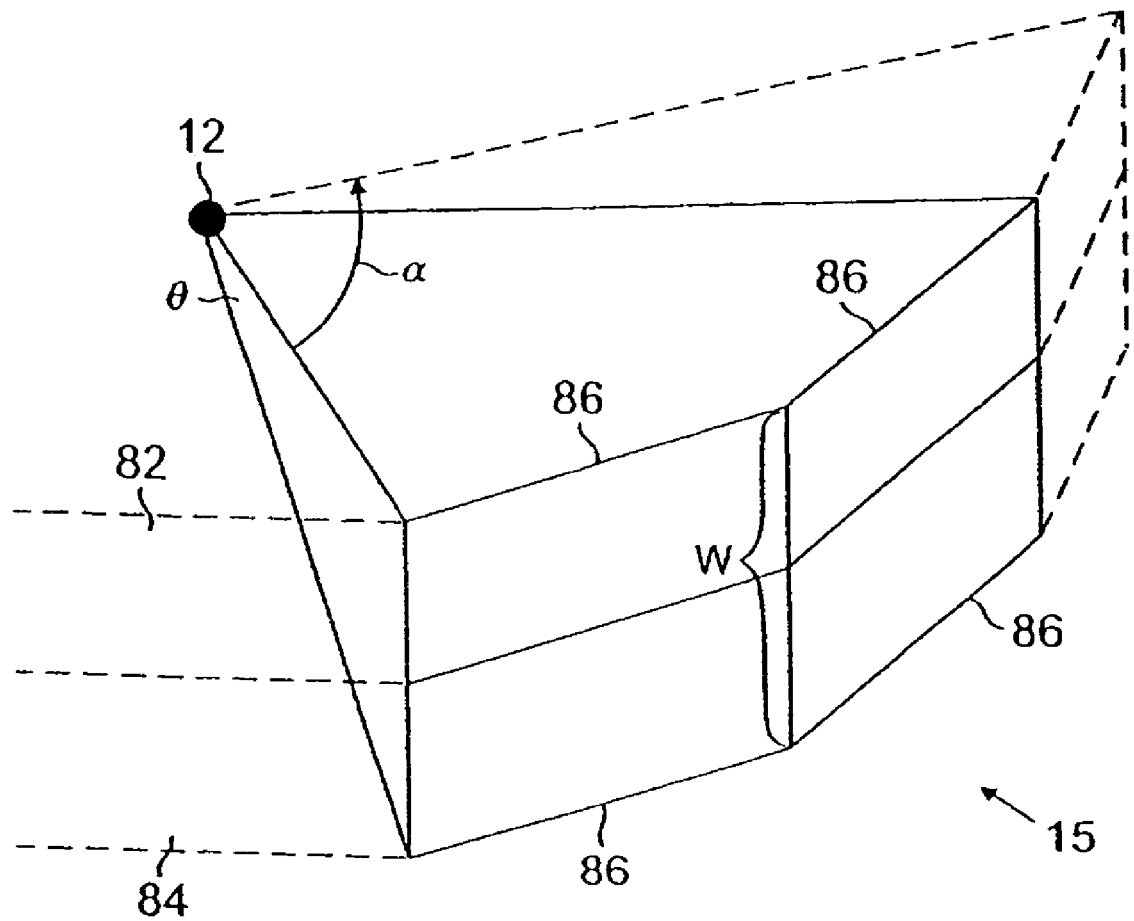
FIG. 6 is a schematic illustration of a portion of a cone beam and a detector array that may be used in the embodiment of FIG. 2.

As mentioned above, one or more collimators 12a may be provided between the X-ray source 12 and the object 13 to collimate the X-ray beam from each source 12 into a desired shape. The X-ray beam may be collimated into a horizontally diverging beam, such as a cone beam or a fan beam, for example. Here, the term "cone beam" refers to a two dimensional, diverging radiation beam, such as a radiation beam that diverges horizontally and vertically. The cone beam need not be a mathematical cone; it may be an arbitrarily shaped cone with a cross-section having an outer edge with a rectangular, square, circular or elliptical shape, for example. FIG. 6 shows a portion of rectangular asymmetric cone beam 80 intercepting a portion of a two dimensional detector array 15. If a circular cone beam is used, data collected from semi-circular portions of the circular cone beam proximate the edge of the circle would typically be discarded. The use of a rectangular cone beam instead of a circular cone beam avoids exposure of the object 13 and its contents to this extra radiation that is typically not be used in imaging.

Here, the term "fan beam" refers to a diverging radiation beam having essentially only one dimension, such as a horizontally diverging radiation beam. Since a cone beam covers more volume of the cargo container per unit time than a fan beam, use of a cone beam enables faster scanning than a fan beam. While a fan beam diverges somewhat in a second dimension, the divergence is very small as compared to the divergence in the first dimension, as is known in the art.

Collimators (not shown) may also be provided between the object and the detector array 15 to block scattered radiation from reaching the detectors of the detector array.

Figure 1:
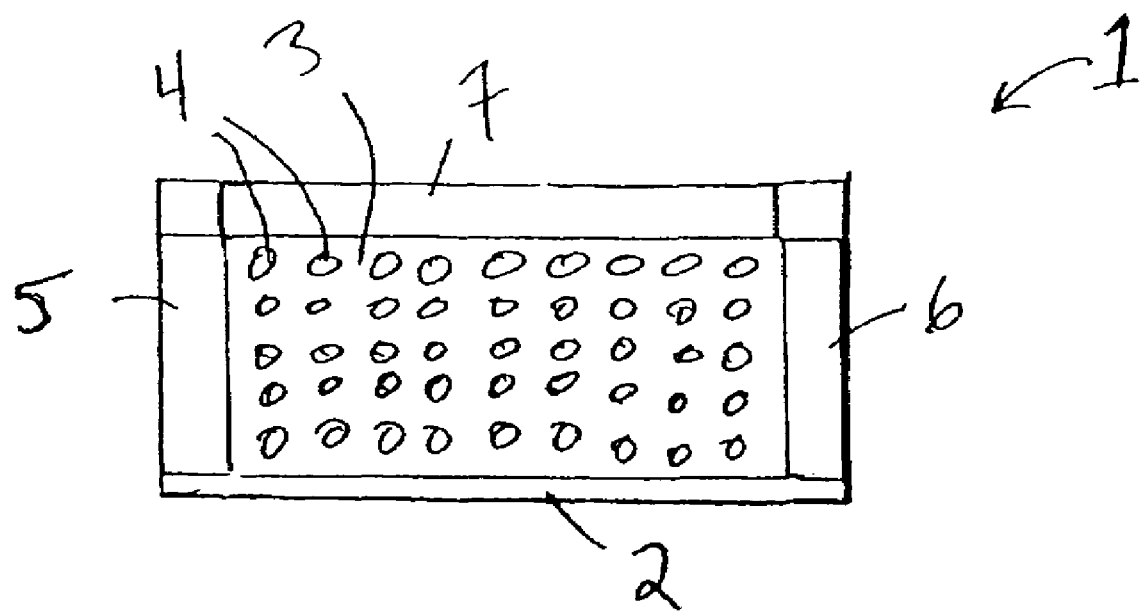
FIG. 1 is a front view of an example of a prior art detector module.

The detector 14 may be a spatial detector. In one example, the detector 14 comprises a detector array 15 comprising a plurality of adjacent detector modules, as shown in FIG. 6. When the X-ray radiation is in the form of a cone beam, the detector array may comprise one or more rows of two dimensional detector modules to detect X-ray radiation transmitted through the object 13. In FIG. 6, a portion of two rows 82, 84 of detector modules 86 are shown. The X-ray source 12, shown schematically as a point source, is aimed at the detector array 15. The object 13 and other components of the scanning unit 10 are not shown for ease of illustration. Each two-dimensional detector module 86 comprises a plurality of rows and columns of detector elements, such as photosensitive elements, in a housing. Certain components of the modules, which are known in the art, are discussed above with respect to FIG. 1. The photosensitive elements may be photodiodes, for example.

The longitudinal or axial width (vertical dimension in FIGS. 1 and 6) of the cone beam 80 at the detector array 15 may approximately correspond to the width "W" of the detector array, as shown in FIG. 6. The cone beam 80 may extend longitudinally over an arc θ of from about 2 degrees to about 30 degrees, for example.

If a fan beam is used, a single row of one dimensional detectors (comprising a single row of detector), may be used. Multiple, closely spaced, parallel fan beams may also be defined by one or more collimators. In that case, a row of one dimensional detectors may be provided for each fan beam.

The detector modules may be an amorphous silicon detector module available from Varian (identified further above), under the tradename Paxscan® 4030HE, for example. Additional details concerning the spatial detector 14 and the Paxscan® 4030HE may be found in the '060 Application, which is incorporated by reference herein and in U.S. Pat. No. 6,848, 808 B1, U.S. Pat. No. 5,970,115 and U.S. Pat. No. 6,800,858, which are assigned to the assignee of the present invention and are also incorporated by reference herein.

The detector 14 (or the detector array 15) detects X-ray radiation transmitted through the object 13. Returning to FIG. 2, the detector 14 is electrically connected to one or more processors or computers 94, which reconstruct the data output by the detector 14 into images, as discussed further below. The computer 94 has one or more inputs 94a to receive the data from the detector 14, and optionally other detectors, also discussed further below. Analog-to-digital converting devices and other electronic components are provided, as required. The computer 94 is connected to a display 96 that displays the reconstructed images. The computer 94 may store the reconstructed images in a database, along with identifying information about each object 13, such as the time and date the object was scanned and the source of the object. The scanning unit 10 may include a bar code scanner (not shown) to read the information and provide the information to the computer 94. The operator of the scanning unit 10 can enter the relevant information though a keyboard or the information can be scanned or otherwise entered automatically. For example, a barcode may be applied to the object 13 before inspection containing such information. The computer 94 is also connected to the X-ray source 12, to the conveyor system and to the driving mechanism of the platform 16, through outputs 94b, to control their operation (the connections are not shown in FIG. 2 to simplify the illustration).

In accordance with one embodiment of the invention, the radiation beam 17 is a "partial" radiation beam that does not completely encompass the object 13. FIG. 7 is a top view of a partial beam system, where one boundary RI of the beam 17 extends beyond a boundary of a cargo conveyance 13 oriented as shown in FIG. 5 and another boundary R2 of the beam intersects the cargo conveyance. Such a radiation beam 17 is referred to as a "partial beam." The cargo conveyance 13 in this example has square ends. The length of a detector array (not shown in this view) is reduced to collect data from the partial beam 17, as compared to the length of a full detector array required to collect data from a "full beam," as discussed further below. The detector array 14 is referred to as a "partial" detector. An example of a full beam system is shown in the '060 Application, where the boundaries of the radiation beam extend beyond the boundaries of the object under examination.

Figure 8:
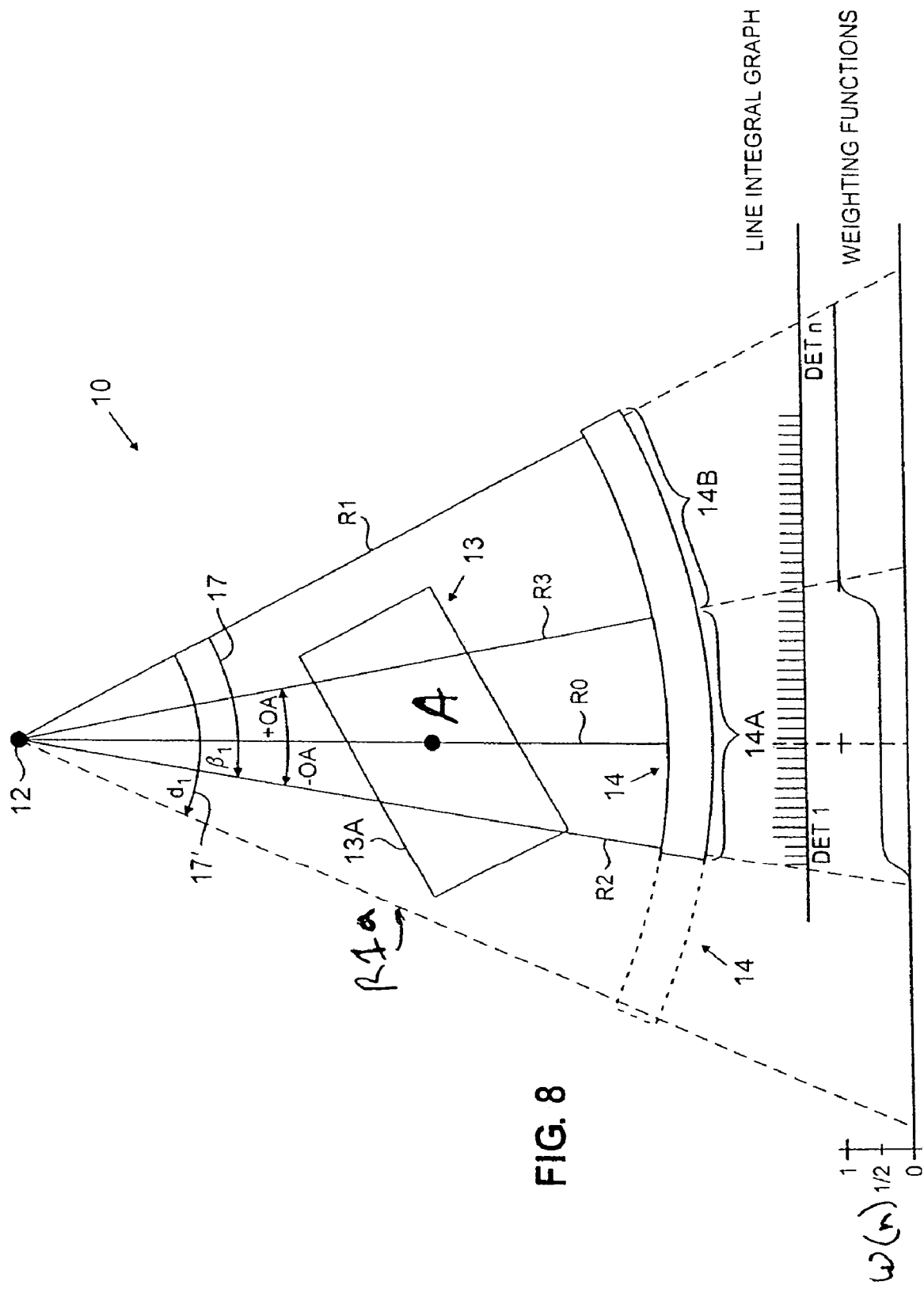
FIG. 8 is a schematic representation of a top view of the scanning unit of FIG. 2, showing a source and a detector in accordance with one embodiment of the invention, wherein the radiation beam is a partial radiation beam and the detector has a reduced length.

FIG. 8 is a schematic representation of a top view of the scanning unit of FIG. 2, adapted to use a partial beam of radiation, as in FIG. 7. The source 12 is shown as a point source. In this example, the cargo conveyance 13 is a cargo container with rectangular ends, oriented as shown in FIG. 5. The source 12 is emitting a partial radiation beam 17 defined between the rays R1 and R2. The ray R1 extends beyond the boundary of the cargo conveyance 13 while the ray R2 intercepts the conveyance, as in FIG. 7. A partial detector or partial detector array 14 is also shown, to capture the radiation beam. A ray R0, from the source 12 through the center of rotation A of the object 13 is also shown. The arc R0R1 is about equal to the arc R0R3. A full beam 17', which is defined by rays R1 and R1a and has an arc d1, is also shown for comparison. An extension 14' of the partial detector array 14 is also shown in phantom, to define a full detector array that would be used to collect the entire radiation beam 17'. The platform 16 and other components of the system 10 of FIG. 2 are not shown to simplify the view.

In the system 10, no radiation is provided through or detected from the left portion 13A of the object 13, which is not intercepted by the radiation beam 17 in the orientation of FIG. 8. No projections are therefore collected through the portion 13A at this point in time. However, as the object 13 is rotated, the portion 13A moves through the radiation beam 17 and projections may be collected. Projections are thereby collected through all points within the object 13, including the portion 13A, as required for CT reconstruction. A complete data set for CT reconstruction may thereby be collected with a partial radiation beam 17 and a partial detector 14 that is a shorter and less expensive detector array 14 than a full detector. To obtain a complete data set, it is necessary to sample at a frequency about twice as fast as the highest spatial frequency, referred to as the Nyquist frequency, as is known in the art. The sampling frequency is not changed in this system as compared to a full beam configuration.

The radiation detected by each detector element of the partial detector 14 is indicative of the attenuation of the radiation by a plurality of infinitesimal three dimensional volume elements surrounding respective points in the cargo conveyance 13 along a ray from the source 12 to the detector element. Each three dimensional volume element is referred to as a voxel. A function of the radiation measured along each of a plurality of rays through an object under examination, which is referred to as measurement line integrals or line integrals, is used in reconstruction algorithms to generate an image.

FIG. 8 also shows a plurality of line integrals in a line integral graph representative of the line integrals measured by the detector elements DET1 through DETn of the detector array 14. The magnitude or value of each line integral may vary due to the type of material in the cargo conveyance 13 (content of each voxel along the ray) and the distance traveled through the cargo conveyance 13 by the radiation detected by each detector element, as is known in the art. Lower density materials result in shorter line integrals than denser materials. If the content of the object 13 is uniform, the line integrals will also be shorter where the distance traveled through the object 13 is shorter.

As mentioned above, a ray R0 passes through the center of rotation of the object 13 and intercepts the detector array 14. There are "overlap angles" +/−OA about the ray R0, between the rays R0R2 and R0R3, respectively, within which detector elements defining a region 14A of the detector array 14 measure twice as many line integrals through the cargo conveyance 13 as detector elements 14B outside of the overlap angle +/−OA, because the detector elements within the overlap angle +/−OA receive two nearly identical projections resulting in measurement of line integrals at nearly exactly opposite directions through the cargo conveyance 13, as the convey-ance is rotated about 360°. The first line integral is obtained when the cargo conveyance 13 is in a first orientation and the second line integral is obtained when the cargo conveyance is in a second orientation rotated about 180° with respect to the first orientation. The detectors within the region 14B, which are outside of the overlap angle +/−OA, only receive projections along line integrals through section 13A, when the cargo conveyance 13 is in one orientation.

To compensate for the different number of projections through the object 13 measured by the detector elements 14A within the overlap angle +/−OA and the detector elements 14A outside of the overlap angle, different weighting values may be applied to the measured line integrals during processing. An example of a Weighting Function graph is also shown in FIG. 8. In this example, the weighting function W(n) for line integrals measured by the detectors 14A within the overlap angle +/−OA, where twice as many line integrals are measured than are measured outside of the overlap angle, is ½, while the weighting function W(n) for detectors 14B outside of the overlap angle +/−OA, is 1. A weighting function W(n) of ½ results in an averaging of the line integrals measured by the detectors 14A. Since CT is sensitive to sudden changes (step functions) in data, the Weighting Function W(n) preferably changes gradually for detector elements proximate the boundary of the region of the overlap angle +/−OA, as shown in FIG. 8. The curves of the transition regions may be arbitrary, as long as they have smooth and continuous derivatives. For example, the Weighting Function W(n) for the detector DET 1 should be zero. The Weighting Function W(n) may increase smoothly from 0 to ½ for the detectors within the region 14A, and from ½ to 1 for the detectors in the region 14B. The weighting function W(n) should sum to 1 for rays symmetric to R1.

The radiation beam 17 may have any arc β less than the arc $\alpha_1$ of a full beam. The relationship between the extent of the partial beam 17 (R1R2) and the corresponding full beam 17' (R1R3), or the Fan Fraction (Arc of Actual Beam (R1R2)/Arc of full beam (R1R3)) may be expressed as follows:

Fan Fraction=½+(R0R2)/2(R0R1), where R0R2 is the overlap angle.

For a full beam 17', the Fan Fraction equals 1. R2 is aligned with R3, and the overlap angle R0R2 is half of the arc R0R1, which is the same as the arc R0R3.

For a three-quarter beam, for example, the Fan Fraction=¾. The overlap angle R0R2 is equal to (R0R1)/2. The detector array 14 may be three-quarters of the length of the detector array 14, and the arc of the beam 17 may be three-quarters of the arc of the beam 17. This configuration is shown in FIG. 8.

For a half beam, the Fan Fraction=½ and there is no overlap angle. In this case, the ray R3 passes through the first detector Det1.

The greater the overlap angle OA, the less the error but the more expensive the detector array. In designing a partial beam/partial detector system in accordance with this embodiment, the expected error may be balanced with the cost of providing a longer detector array.

As mentioned above, the beam 17 may be a fan beam or a cone beam. If the beam 17 is a fan beam, the detector 14 may be one-dimensional. The line integrals will be along the one dimension of the fan beam, as will the Weighting Function W(n), as shown in FIG. 8. If the beam 17 is a cone beam, the detector 14 may be a two-dimensional detector, as shown in FIG. 6. The line integrals will be measured in two-dimensions and Weighting Functions W(n) are provided for each dimension. The shape of the Weighting Function W(n) may be the same in the second dimension as in the first dimension shown in FIG. 8, with the addition of a second symmetric weighting function perpendicular to the first weighting function. The shape and arc of the beam 17 may be defined by suitable collimation, as discussed above and is known in the art.

Fan beam image reconstruction may be used for any Fan Fraction between ½ and 1. Partial fan beam data may be reconstructed using techniques similar to those used for the extension of partial fan data in well-known single slice fan beam CT, as is known in medical CT by use of suitable weighting functions, as discussed above. See, for example, U.S. Pat. No. 5,692,507, which is assigned to the assignee of the present invention and is incorporated by reference herein. For partial cone beam reconstruction of partial cone beam fractions between ½ and 1, the partial cone beam data is extended to full cone beam image data and is then reconstructed using a full cone beam reconstruction algorithm well known to those of ordinary skill in the art, such as the Feldkamp cone beam reconstruction technique, for example. Known reconstruction algorithms compensate for the divergence of the fan or cone radiation beam through the object.

Figure 9:
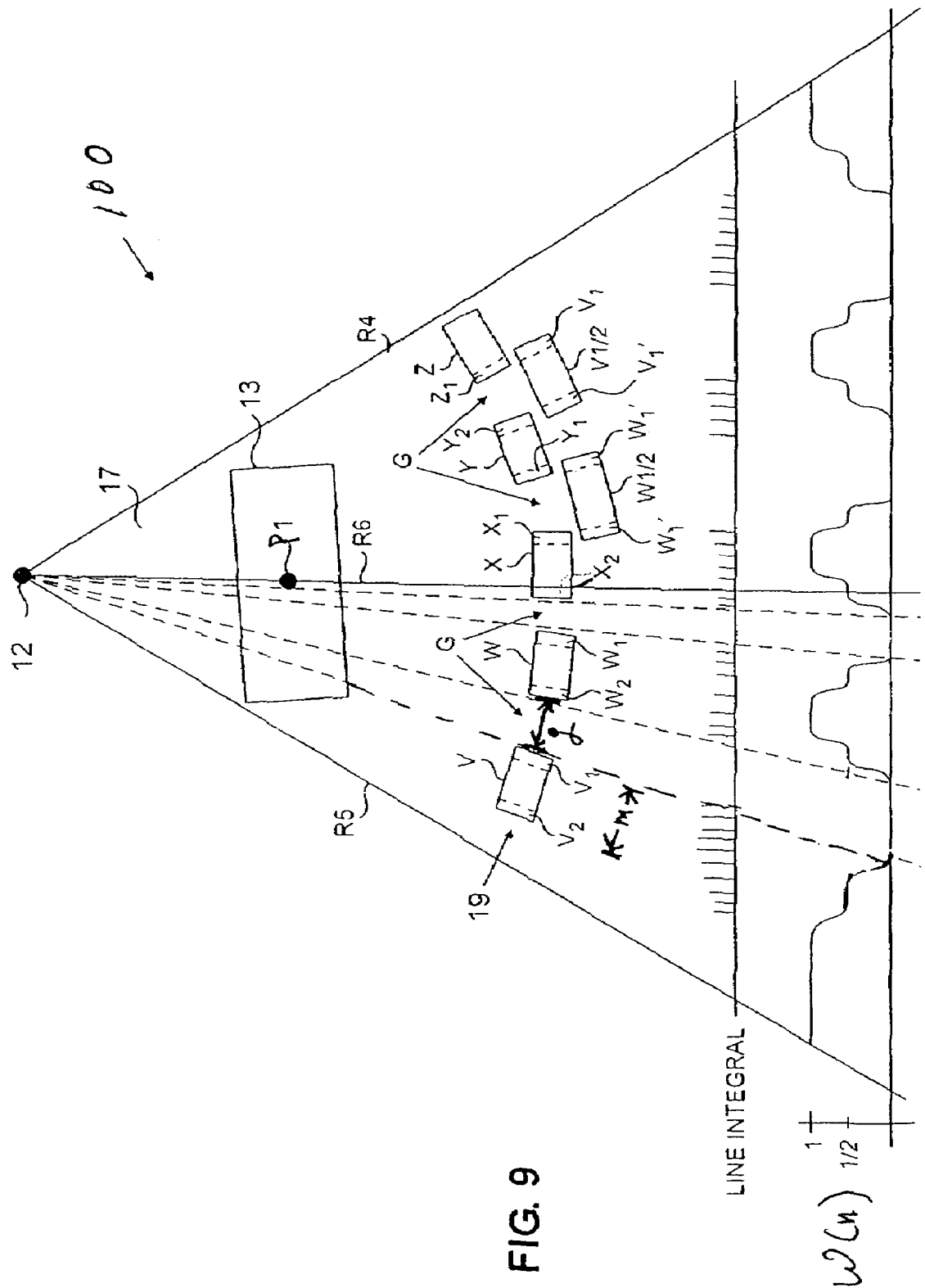
FIG. 9 is schematic representation of a top view of the scanning unit of FIG. 2, showing a source and a detector in accordance with another embodiment, where gaps are provided along the length of a detector.

FIG. 9 is a schematic representation of a top view of the scanning unit 10 of FIG. 2, in accordance with another embodiment of the invention. In the illustrated example, where the scanning unit is numbered 100, the partial detector 19 comprises five (5) detector modules V, W, X, Y, Z, separated by four gaps G. In an actual system, additional detector modules and gaps may be provided. The point source 12 and the object 13 are also shown, as in FIG. 8. The source 12 emits a radiation beam 17 defined by two rays R4, R5. In this example, the radiation beam 17 is a full radiation beam that extends beyond both edges of the object 13. The beam could be a partial beam intercepting one side of the object, as well. A ray R6 extends from the source 12 through a center of rotation of the object 13 and through the detector module X. Preferably, one detector module on one side of the array 14, here detector module Z, extends beyond an outside edge of an object to capture radiation that does not pass through the object. Another detector module on another side of the detector array, here detector module V, need not extend beyond the corresponding edge of the object, as shown. Since fewer detector modules are used than in a full detector array, the cost of a scanning system 100 may be reduced. In addition, detector electronics may not be exposed to radiation or as much radiation as in a full detector array, as discussed further below. This may decrease shielding requirements, decreasing costs. Maintenance costs may be decreased, as well. It is noted that FIG. 9 is not drawn to scale.

Two detector modules V, W are to the left of the ray R6 and two detector modules Y, Z are to the right of the ray R6. The detector module X is positioned such that the ray R6 intercepts the module X between the center and a left end of the module. No data is collected within the gaps G, as indicated by the line integrals in the Line Integral graph shown on FIG. 9. To compensate for the lack of data collected at those locations, the detector modules V-Z and the gaps G are positioned such that projections of mirror images V', W' (shown in phantom) of the left detectors V, W onto the right side of the ray R6 at least coincides with (fills) the gaps G on the right side of the ray R6. In this way, the data that is not collected by the right detector modules X, Y, Z is collected by the left detector modules V, W, as the object 13 is rotated. All line integrals through the object are thereby measured at least once, and some are measured twice. As above, the sampling frequency of the measurements of the line integrals is the same as in a system with a detector without gaps. Only the number of times certain line integrals are measured is changed.

Preferably, the widths of the gaps G are less than the widths of the detector modules so that in the projection of the mirror image, V', W' also overlap portions of the detector modules X, Y, Z, as shown. In particular, the regions W1', W2', V1', V2', overlap respective regions X1, Y1, Y2, Z1 of the detector modules Y and Z. Corresponding regions V1, V2, W1, W2 of the actual detector modules V, W are also indicated. The regions W1', W2', V1', V2' measure the same line integrals as are measured by the regions X1, Y1, Y2, Z1 of the detector modules X, Y, and Z, respectively. Twice as many line integrals are therefore measured through the corresponding portions of the object 13 by the overlapping portions of the detector modules.

A Weighting Function W(n) is therefore used to compensate for this extra data and produce images with less error, as in the embodiment of FIG. 8. The weighting function has a value of ½ at the centers of the overlapping regions V2, V1, W2, W1, X1, Y1, Y2, Z1 to average the two line integrals measured due to the overlap of the portions of the detector modules. The Weighting Function W(n) has a value of 1 outside of the overlapping regions, where line integrals are measured once. As above, it is preferred that the values of the Weighting Function W(n) transition smoothly between regions so that it has smooth and continuous derivatives.

The detector modules V, W, X, Y, Z, are preferably positioned so that the width of the overlap on each side of each module (except for the module Z on the end of the array, which is only overlapped on one side) by a projected mirror image is equal to ½ (m-g), where m is the width of the section of the module including the detector elements in that dimension and g is the selected width of the gap along that dimension. The width m of the detector module V and the width g of the adjacent gap G is shown in FIG. 9. For example, if the detector modules are Paxscan® 4030 HE modules available from Varian, the detector elements (detector elements 4 in FIG. 1) are in a section that is 40 mm wide and 30 mm high. If the selected gap is 30 mm, then the overlap of the detector elements is preferably 5 mm on each side of the module. In addition, the ray R6 through the center of rotation of the object 13 preferably intersects the module X in a location X2 that is the same distance from the left edge of the module, as the width of the overlap, as shown in FIG. 9. It is noted that the electronics sections of the detector modules, such as electronics sections 5, 6, in FIG. 7, are considered to be part of the gaps G.

The larger the selected gaps G, the fewer detector modules are required. However, multiple measurements of line integrals reduces error. In designing a detector array in accordance with this and the related embodiments discussed below, the expected error may be balanced with the cost of providing additional modules.

While equal overlap on each side of a module is preferred, it is not required. For example, instead of overlapping regions of 5 mm on each side of a module, as above, the overlapping regions Y1 and W1' may have a width of 6 mm and the overlapping regions Y2 and V1' may have a width of 4 mm, for example.

Figure 10:
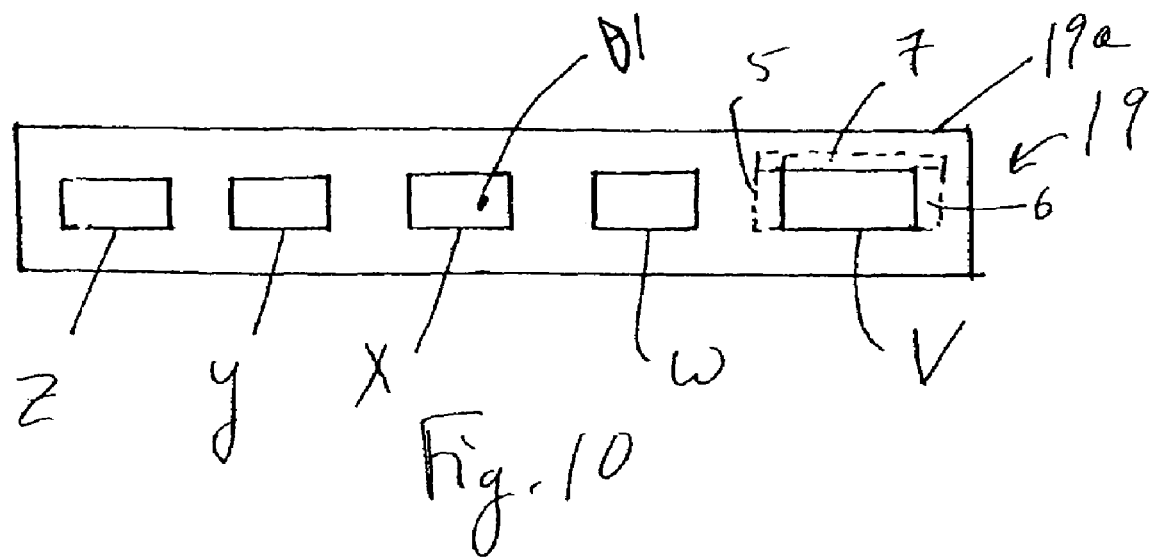
FIG. 10 is a front view of a one dimensional detector array for use in the embodiment of FIG. 9.

FIG. 10 is a front view of the detector array 19 of FIG. 9 for use in detecting a fan beam of radiation. The detector modules V, W, X, Y, Z, and the gaps G, are shown, supported by a frame 19a of aluminum, iron or plastic, for example. Point D1, which indicates the intersection of a ray R6 from the source 12 through the center of rotation P1 of the object 13 and onto the detector module X of the detector array 19, is also shown. The detector array 19 may be curved or flat.

Figure 11:
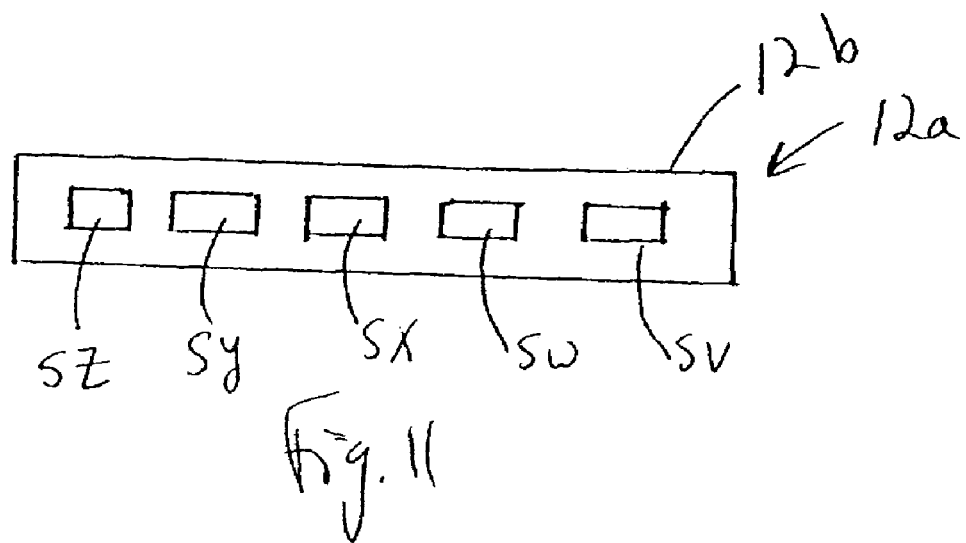
FIG. 11 is a front view of a collimator for use with the detector array of FIG. 10.

FIG. 11 is a front view of a collimator 12a that may be used to define a fan beam of radiation that may be detected by the detector array 19 of FIG. 10, after interaction with the object 13, in the example of FIG. 9. The collimator 12a comprises a body 12b of shielding material, such as lead or tungsten, with a plurality of slots SV, SW, SX, SY, SZ. The slots SV through SZ each have a shape and location corresponding to the shapes and locations of the detector modules V, W, X, Y, and Z of FIG. 10, respectively. The number of slots is the same as the number of detector modules in the array 19. The height and width of the slots SV through SZ are such that each beam defined by each slot diverges over the distance from the collimator 12a to each detector module V through Z, respectively, to fill the window of the respective detector module to irradiate all of the detector elements. The slots SV through SZ are configured so that the electronics portions 5, 6, 7 of each detector module V through Z, shown in phantom only on the module V for ease of illustration, are not irradiated. Since the fan beam is not a continuous fan beam, such a beam may also be referred to as a partial beam. In addition to or instead of the collimator 12a, a collimator may be provided in front of the detector array 19. Such a collimator would be proportionately larger to collimate the diverging radiation beam.

Figure 12:
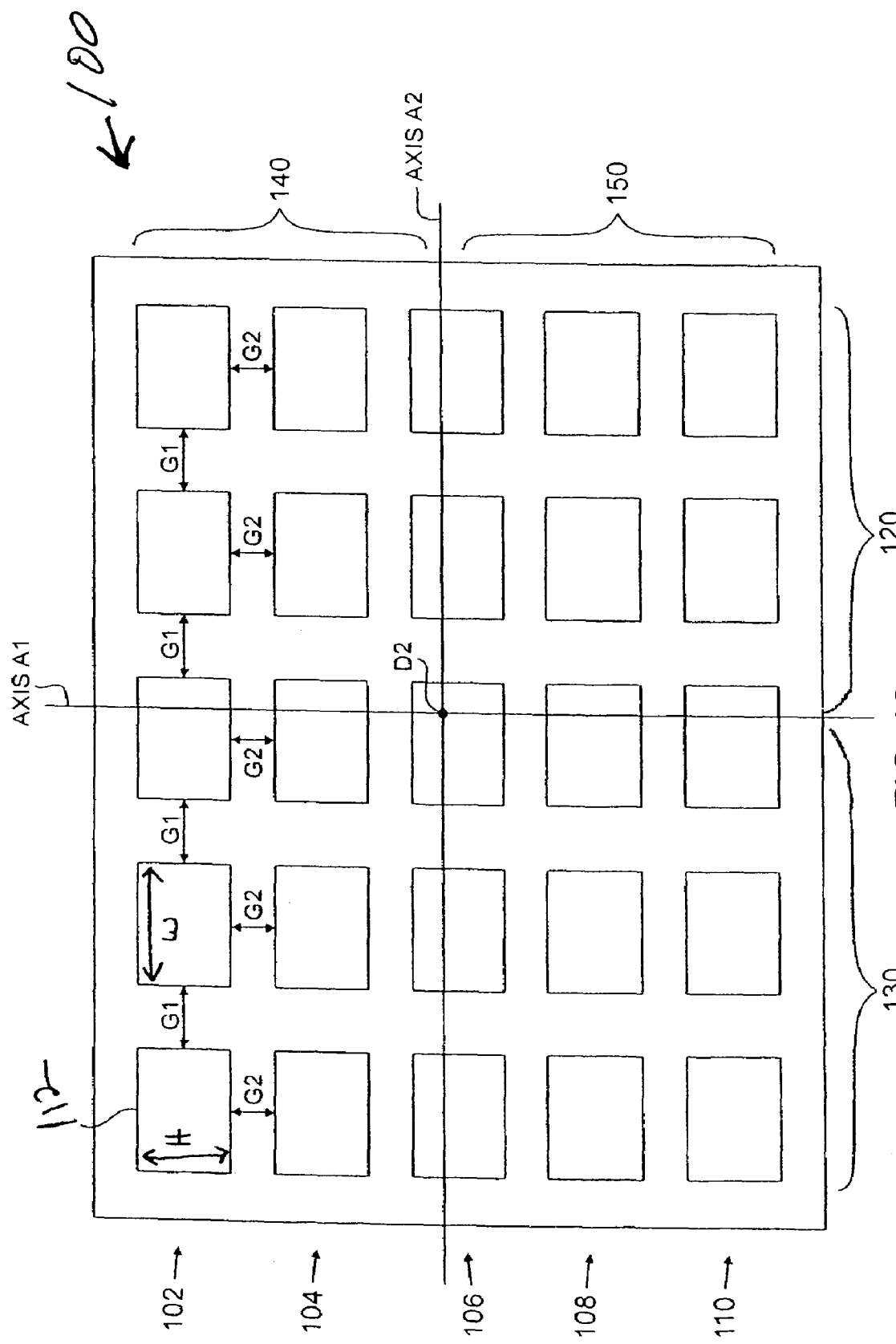
FIG. 12 is a front view of a two dimensional detector array for use in the embodiment of FIG. 9.

FIG. 12 is a front view of an example of a detector array 100, as viewed from the position of the source 12 of FIG. 9, for use in detecting a cone beam of radiation. The detector array 100 comprises a plurality of rows of detector modules 112. Five rows 102, 104, 106, 108, 110 are shown. Gaps G1, G2 are provided between the rows 102 through 110 and between the detector modules 112 along a row, respectively. Only the gaps G1, G2 between modules along the row 102 and between modules in adjacent rows 102, 104, respectively, are shown, for ease of illustration. A point of intersection D2 of the ray R6 of FIG. 9 from the source 12 through the center of rotation P2 of the object 13 and upon the detector array 100, is shown. An axis A1 parallel to the vertical axis of rotation of the platform, as viewed from the source 12, is drawn perpendicular to the Ray R6, dividing the detector array into two sides 120, 130. A mirror image of the detector modules 112 on the side 120 of the detector array 100, projected onto the side 130 of the array (about the axis A1), fills the gaps G1 on the side 130 of the array, as above. Preferably, there is overlap of the modules, as well. A lateral axis A2 of the detector array 100, which is perpendicular to the Ray R6, is also shown, dividing the detector array into two sides 140, 150. A mirror image of the detector modules 112 on the side 140 projected onto the side 150 of the array (about the axis A2), fills the gaps G2 on the side 150. Preferably, there is overlap of the modules here, as well.

The positions of the detector modules and the widths of the gaps G1 across each row may be determined as discussed above with respect to FIG. 12. The widths of the gaps G2 may be similarly determined. If the detector modules are Paxscan® 4030HE detector modules from Varian, the height H of each module is 30 mm. If a gap G2 of 20 mm is selected, then the preferred overlap of detector modules in a projection of the mirror image of the upper section 140 onto the lower portion 150 is 5 mm on the upper and lower portions of each detector module.

Figure 13:
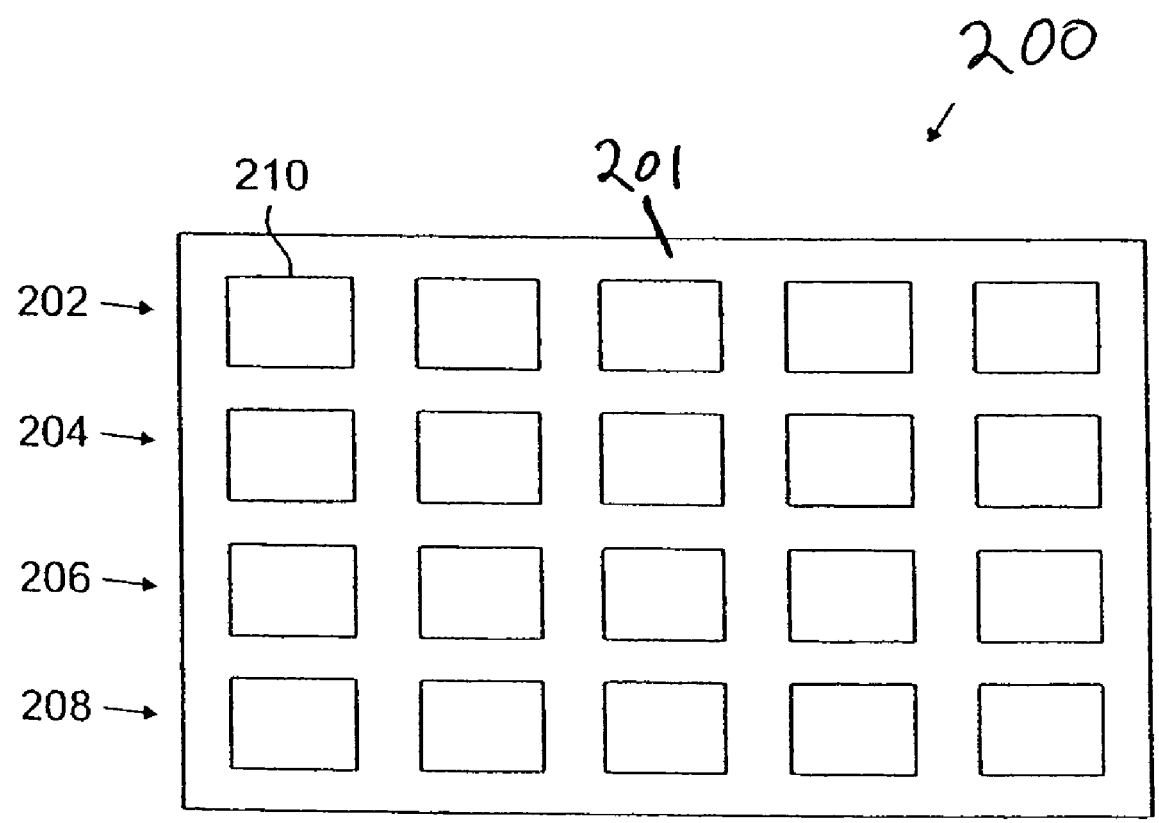
FIG. 13 is a front view of a collimator for use with the detector array of FIG. 12.

FIG. 13 is a front view of a collimator 200 for use with the two dimensional detector array 100 of FIG. 12. As above, the collimator 200 comprises a shield 201 of shielding material, such as lead or tungsten, defining a plurality of rows 202, 204, 206, 208 of slots 210 through the shielding material. The number of rows of slots and the number of slots per row correspond to the number of rows of the detector array 100 and the number of detector modules 110 per row. The size, shape and position of the slots depends on the size, shape and position of each detector module 110 and the distance from the collimator 200 to each detector module 110. As above, the height and width of each beam at each detector module is preferably about the same as the area of the detector elements of each detector module, and the electronics sections 5, 6, 7 are not irradiated. In addition to or instead of the collimator 200, a collimator may be provided in front of the detector array 19 (see FIG. 9). Such a collimator would be proportionately larger to collimate the diverging radiation beam.

A two dimensional Weighting Function W(n) may be used, similar to that described above with respect to the one dimensional detector array 19 with gaps of FIG. 9. The Weighting Function W(n) may have a value of ½ for overlapping regions of detector modules in the same column, and a value of 1 outside of the overlapping regions, in both dimensions. As above, it is preferred that the Weighting Function W(n) transition smoothly so that it has smooth and continuous derivatives.

During operation of the scanning unit 10 of FIG. 2, an object 13 to be inspected is placed on the first conveyor belt 64. The first conveyor belt 64 and the third conveyor belt 72 (on the platform 16, as shown in FIG. 4) convey the object 13 into position on the platform 16, at ground level 0 (FIG. 2). An operator may then secure the object 13 to the platform 16 by ropes, belts, and/or clamps, for example. The object 13 may be automatically secured, as well. The X-ray source 12 is activated to emit an X-ray beam collimated into a cone beam 17 of radiation focused on the bottom portion of the object 13. A fan beam may be used, instead. The platform 16 is activated to rotate and recess into the cavity 18 below the platform 16. As the platform 16 rotates and recesses, the cone beam 80 sweeps the object 13 and its contents in a helical pattern. When the platform 16 reaches its lowest level −10, as shown in FIG. 3, the scanning cone beam is at the top of the object 13. The platform 16 then rises (continuing to rotate in the same direction or in the opposite direction, depending on the driving mechanism 20), and continued scanning may optionally be performed.

In one implementation, the distance between the source 12 and the object 13 and the object and the detector 14 may be from about 1.5 to about 2 times the maximum radius of the object. The radiation beam 17 is a cone beam extending longitudinally over an arc θ of about 2 to about 30 degrees, and preferably about 15 degrees. The cone beam 17 may extend laterally over an arc α of about 45 to about 80 degrees, for example. (See FIG. 6, for example). About 45 degrees is preferred. The platform 16 may then be moved in each direction for one minute. The platform 16 may be rotated 2-4 times during movement in one direction, for example. About 300 to about 1,000 projections per each complete rotation of the platform 16 may be taken for CT reconstruction, for example. Further details concerning operation of the rotating platform 16 is provided in the '060 Application, which is incorporated by reference, herein.

After the object 13 has been raised and/or lowered a desired amount while being scanned, rotation and vertical motion of the platform 16 is stopped and the source 12 is turned off. The data received by the detector 14, along with the angular and vertical coordinates (cylindrical coordinates) of the platform 16, are provided to the computer 94 and used to reconstruct volumetric computed tomography ("CT") images. As mentioned above, reconstruction algorithms for reconstructing volumetric images based on scanning with a partial cone beam or a partial fan beam are known in the art.

Reconstructed images may be analyzed by computer 94 and/or visually by an operator of the system. If desired, the object 13 may be scanned again. When scanning is completed, the object 13 is conveyed from the platform 16. If the object 13 passed inspection, the platform 16 may be aligned with the first exit path along the second conveyor belt 68, as shown in FIG. 4. The second and third conveyor belts 68, 72 are activated and the object 13 is conveyed off of the platform 16 and out of the scanning unit 10.

If the object 13 did not pass inspection, it may be scanned again on the platform 16. The rotational and vertical movement of the platform 16 is resumed and the source 12 is turned on. The object 13 may be readily scanned as many times as required. Subsequent tests can be conducted at slower rotational and/or vertical movement speeds of the platform 16 or higher dose rates of the X-ray beam 80, than in the initial scan, for the entire object or just while scanning suspicious portions of the object. If the object 13 has been removed from the platform 16 before it is determined that additional scanning is necessary, the second and third conveyor belts 68, 72 may be reversed to return the object 13 to the platform 16.

Additional information useful in identifying contraband may also be obtained by selectively detecting transmitted energy in different energy ranges. Filters (not shown) may be selectively provided in front of the detector 14 of FIG. 2 to improve the energy sensitivity of the detector for a particular energy range. For example, the filters may be configured to block radiation transmitted through the cargo below a certain threshold. An example of a detector that is sensitive over a broad energy range and may be used in the present invention is described in U.S. Pat. No. 6,800,858 B1, which is assigned to the assignee of the present invention and is incorporated by reference herein. Commercially available scintillation based detectors comprising photomultipliers, semiconductor based detectors and gas ionization based detectors sensitive to particular energy ranges may also be used.

As is known in the art, the interaction of X-ray radiation with different materials, including contraband such as explosives, is dependent in part on the energy of the X-ray radiation. Additional information useful in identifying contraband may therefore also be obtained by scanning the object 13 with two or more different energy distributions. One of the energy distributions may be one with an average energy in which the primary interaction of the X-ray radiation with the object is Compton scattering. The other energy distributions may have progressively higher average energies that will cause progressively more pair production and less Compton scattering.

For example, when examining larger objects (having a diameter greater than about 5 feet (about 1.5 meters)), two energy distributions may be provided by X-ray sources with accelerating potentials of 4 MV and 10 MV, or 6 MV and 18 MV or higher, for example. At peak energies of 4 MeV and 6 MeV, the X-ray radiation will predominantly cause Compton scattering. Pair production will only be a small fraction of resulting X-ray interaction. At peak energies of 10 MeV or 18 MeV or higher, more pair production is induced. Compton scattering takes place as well.

For smaller objects, such as luggage, X-ray tubes having accelerating potentials of about 200 KV and 90 KV, for example, may be used to generate X-ray radiation having peak energies of 200 KeV and 90 KeV, respectively. The higher peak energy induces more Compton scattering while the lower peak energy induces more radiation by the photoelectric effect, as is known in the art.

Different X-ray sources emitting X-ray radiation with different peak energies may be used. Corresponding detectors aligned with each source may be provided, as well. In FIG. 2, for example, a second source 92 is shown in phantom. A second detector 98 is also shown in phantom aligned with the source 12a and the object 13. The first and second sources 12, 92 and the first and second detectors 14, 98 may be stacked, as shown schematically in FIG. 1. The radiation may be emitted by each source 12, 92 in alternating pulses to reduce interference due to scatter. One or more pairs of sources and detectors may also be diametrically arranged around the platform 16. A source/detector pair may be arranged along a diameter perpendicular to, or at another large angle with respect to, to the diameter defined by the source 12 and detector 14 in FIG. 2, to reduce cross talk and interference. For example, a second source/detector pair may be provided along an axis of the first and second conveyor belts 64, 68. The additional source/detector pair may be positioned high enough above the level of the conveyor belts 64, 68 that the object 13 may be conveyed along the belts. The platform 16 may be raised to a sufficient height to be scanned by all of the sources provided. Instead of providing additional detectors aligned with each source, a single detector or detector array could be moved into alignment with an active source.

The additional sources may be linear accelerators and/or X-ray tubes emitting radiation at different peak energies. The additional sources may also include one or more radioisotopes. For example, one of the sources may be Cobalt-60, which emits essentially monoenergetic radiation at multiple energy levels. The second source 92 may also be a source of another type of radiation, such as a source of neutrons. Since different types of radiation may interact differently with certain materials, use of a different type of radiation to examine the object 13 may provide additional information that may be useful in identifying the contents of the object.

Alternatively, the source 12 may be capable of selectively emitting X-ray radiation at two or more different energy distributions. A description of a suitable source may be found in U.S. application Ser. No. 10/957,212 for a Standing Wave Particle Beam Accelerator, filed on Oct. 1, 2004, which is assigned to the assignee of the present inventor and is incorporated by reference herein. Linear accelerators that can emit X-ray radiation at two or more different energy distributions are also described in U.S. Pat. Nos. 6,366,021 B1, 4,382,208 and 4,400,650, for example, which are also assigned to the assignee of the present invention and are incorporated by reference, herein. If it is desired to use more than two energy distributions, the platform 16 may be raised and lowered multiple times. The object 13 may also be illuminated by multiple energies from a single source 12 by selectively moving an energy selective filter between the source and the object.

One energy distribution may be emitted while the platform is moving in one vertical direction and the other energy distribution may be emitted while the platform is moving in the opposite vertical direction. A pause may be provided in the motion of the platform 16 before changing vertical direction, while the energy is being changed. While concerns over induced radioactivity might limit the upper range of the highest peak energy used to about 20 MeV, it may still be desirable to use higher energies in small area interrogation. For example, if a suspicious region is identified at a lower energy, a higher energy may be used to scan the suspicious region.

As mentioned above, the detector of FIG. 2 may be a spatial detector that detects the radiation transmitted through the object 13 at each energy distribution. Alternatively, an energy sensitive detector 99 may be provided behind the spatial detector, as shown in phantom in FIGS. 2 and 4. The second, energy sensitive detector 99 may be a detector array. When the radiation beam is in the form of a cone beam, the detector 99 may comprise one or more rows of two dimensional energy sensitive detectors, in the form of detector modules.

The second detector 99 may be responsive to the higher energy X-ray radiation transmitted through the object 13 and through the first detector 14. Preferably, the first detector 14 has an efficiency up to about 50%, so that a sufficient amount of X-ray energy will pass through the first detector to be detected by the second detector. The first detector 14 may have higher efficiencies and still allow sufficient X-ray energy to pass through, as well. If the first detector array 14 is a partial detector with gaps, as in the embodiment of FIGS. 9-13, the second detector 99 may have corresponding gaps, as well.

Instead of providing a separate energy sensitive detector array 99, two dimensional energy sensitive detectors in the form of detector modules, for example, may also be provided among the two dimensional detectors of the first detector array 15. Filters may be provided between the detectors 14, 99 to remove radiation below a certain threshold, to improve the sensitivity of the energy sensitive detector array to higher energies, if desired.

The detectors of the second detector array 99 may each comprise scintillators coupled to a photomultiplier tube, for example, as is known in the art. Pulse Height Analysis ("PHA") may be used to analyze the data from the energy sensitive detectors, as is known in the art. The scintillator may be a cesium iodide scintillator, for example.

Images may be prepared based on data collected at each peak energy. Separate data points may be derived from scanning at each respective energy distribution, for each voxel of the object 13. Analysis of data at different energies and images derived from data at different images are discussed further in the '060 Application, which is incorporated by reference herein.

If the object is adequately secured to the platform, the platform may be rotated about and translated along a non-vertical axis, as well. In addition, the axis of rotation and the axis along which the platform is translated, need not be the same. These variations are also discussed in more detail in the '060 Application, which is incorporated by reference herein.

Figure 14:
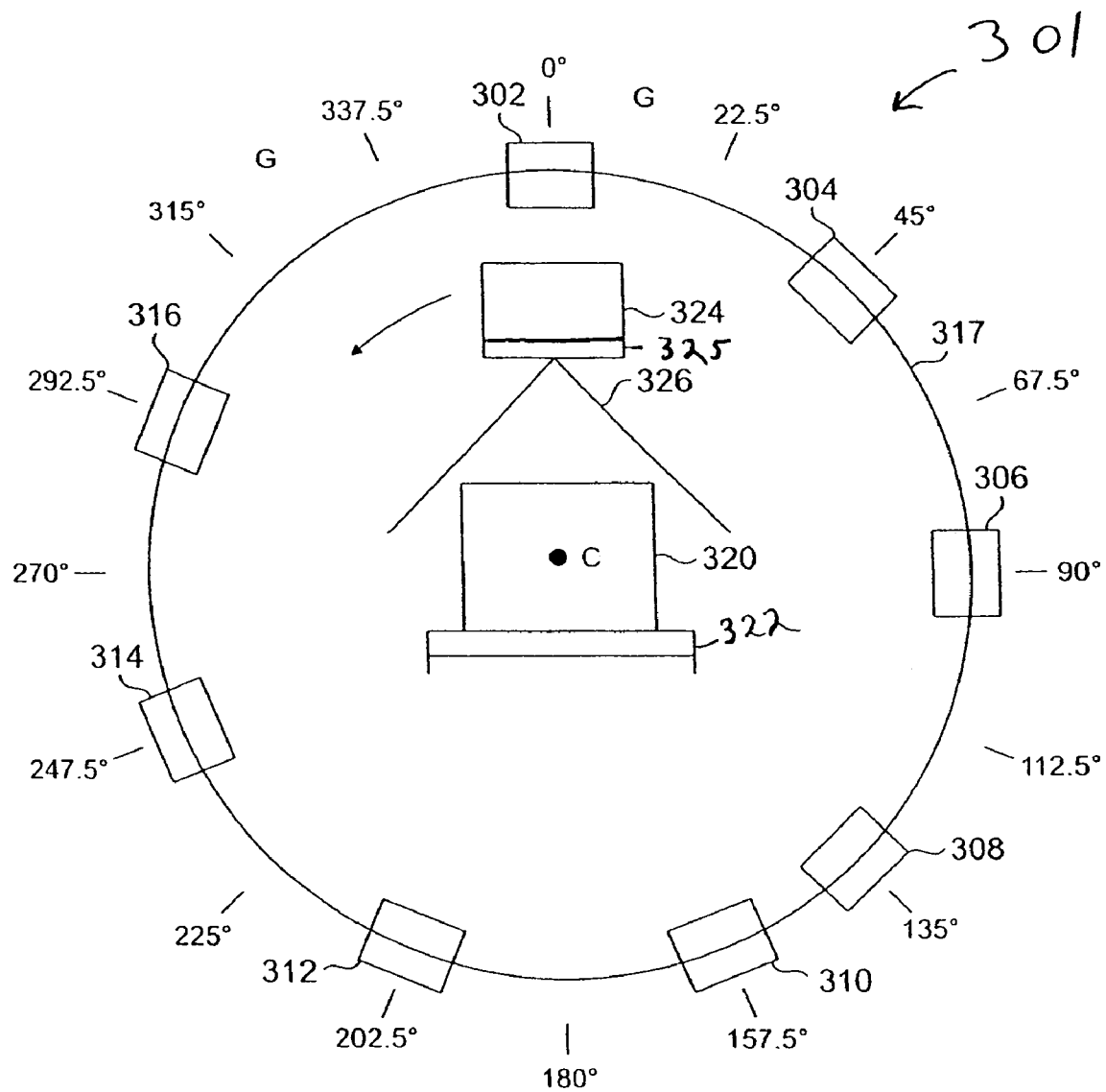
FIG. 14 is a schematic representation of a front view of a fourth generation scanning unit in accordance with an embodiment of the invention.

The techniques described herein to reduce the number of detector modules used in a detector array by providing gaps along an expanse of a detector or detector array may be used in any system where at least some line integrals are measured more than once at object positions about 180 degrees apart. For example, in fourth generation CT systems, where detectors completely surround the object in a circle and the source is moved completely around the object in a circle within the detector circle, two identical line integrals are collected through the object. FIG. 14 is an example of a fourth generation CT system 300 in accordance with an embodiment of the invention. Several exemplary detector modules 302 through 316 of a detector array 301 are shown, positioned along a circle 317 with a center C. In this example, the center C of the circle 317 corresponds to the center of the object 320, but that need not be the case. Only certain detector modules 302 through 316 are shown for ease of illustration. Gaps G are provided between adjacent modules.

In a simple illustration of the concept in FIG. 14, some detector modules are provided on one side of a diameter through the center C, but not on the opposite side, so that every line integral through the center C of the object is received by at least one detector module, to collect a complete set of data. Since data collection on opposite sides of each diameter is the same, it is not necessary to collect the same data by two different modules. The detector modules 302 and 306 are centered at 0 degrees and 90 degrees, but no modules are centered at 180 degrees and 270 degrees. Detector modules 304 and 310 are centered at 45 degrees and 135 degrees, but no modules are centered at 225 degrees and at 315 degrees. Detector modules 312 and 316 are centered at 202.5 degrees and 247.5 degrees, but no modules are centered at 22.5 degrees and 112.5 degrees. A more accurate example is discussed below with respect to FIG. 15.

Figure 15:
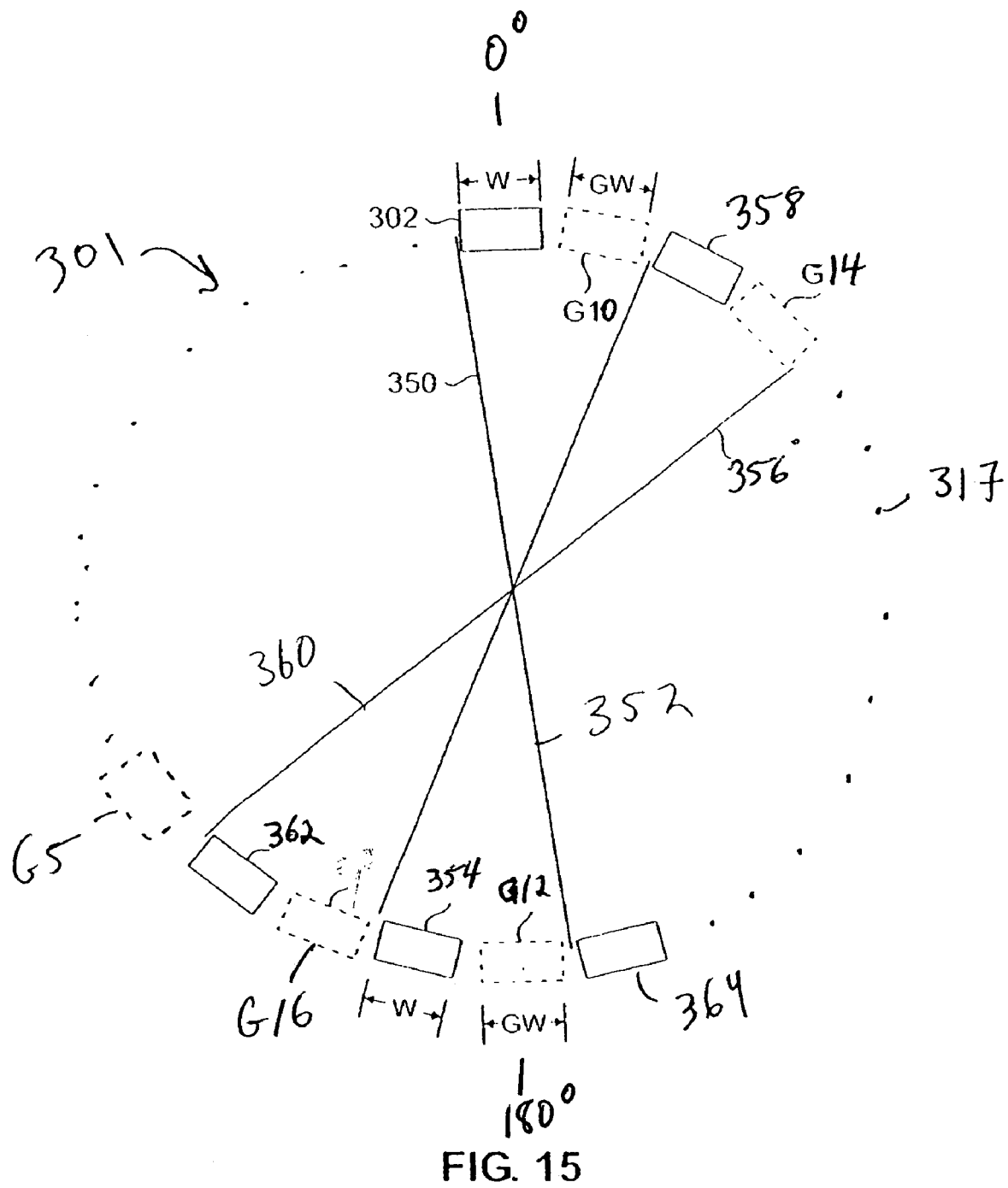
FIG. 15 is a schematic representation of the detector array in FIG. 14, showing certain detector modules in more detail.

FIG. 15 shows several detector modules and gaps in the detector array 301. The detector modules may be arranged so that in a mirror image of a pie-shaped region 350 defined by a module and an adjacent gap, such as the module 302 of FIG. 14 centered at 0 degrees and the adjacent gap G10, projected about 180 degrees around the detector array 301 onto another pie-shaped region 352 comprising a detector module and an adjacent gap, such as the module 354 and the gap G12 centered at 180 degrees, the module 302 at least coincides with the gap G12 and the projection of the gap G10 coincides with or lies within the module 354. Each pie-shaped region extends from one outer edge of one detector to a far edge of the adjacent gap, as shown in FIG. 15. The gaps G10, G12 and other such gaps preferably have widths GW less than widths W of the detector modules 302, 354 so that in the projection of the mirror image, the detector modules overlap both gaps G10, G12 and portions of the adjacent modules. The line integrals not measured in the gap regions G10, G12 are therefore detected by the detector modules 302, 354, respectively. All line integrals through the pie-shaped regions 350, 352 are therefore measured at least once and some are detected twice.

Similarly, another pie-shaped region 356 comprises a module 358 and a gap G14. In a projection of the pie-shaped region 356 about 180 degrees around the detector array 301 onto a corresponding pie-shaped region 360 comprising a detector module 362 and a gap G16, the detector module 358 at least coincides with the gap G16 and the gap G14 coincides with or lies within the module 362. It is also noted that the gap G10 and the detector module 358 also define a pie-shaped region. When projected 180 degrees around the detector array 301, onto a corresponding pie-shaped region comprising the gap G16 and the detector module 354, the module 358 at least coincides with the gap G16 and the gap G10 coincides with or lies within the module 354. Additional detector modules and gaps, such as the module 364 and the gap G5, extend in an alternating fashion around the detector array 301.

Line integrals measured twice due to overlapping portions of the detector modules in the projection, may be averaged by use of a Weighting Function W(n) of one-half, as described above with respect to FIG. 9. Weighting Functions W(n) for portions of detector modules where the line integrals are only measured once may have a Weighting Function W(n) of 1. It is noted that the greater the overlap, and hence the greater the number of line integrals through the object detected more than once, the less error in the measurements. In designing a detector array in accordance with this and other embodiments and configurations of the invention, the expected error may be balanced with the cost of providing additional modules.

As discussed above, the detector modules may be Paxscan® 4030HE detector modules available from Varian. The Paxscan® 4030 is 40 cm wide and 30 cm high. If a diameter of the detector array 301 is 2 meters, 17 Paxscan® 4030HE modules are required to define a complete circular detector array with no gaps. In a detector array with gaps in accordance with an embodiment of the invention at least 9 detector modules but fewer than 17 detector modules are provided. In general, more than half the number of detector modules required in a full detector array are provided so that there is overlap of detector modules in the projection of the mirror images, and therefore at least some multiple measurement of the same line integral through the object. If 9 detector modules are used, the gaps would be about 17 mm and the overlap on each side in the projection would be about 6 mm.

Returning to FIG. 14, an object 320, which may be a patient, is supported on a support 322. A source 324 is movable about a circle concentric with the circle 317 within the detector array 301, to emit a radiation beam 326 to irradiate the object 320 with radiation at all angles. The support 322 may move the object along an axis in a direction perpendicular to the motion of the source 324, in this example out of the page, continuously or incrementally, as is known in the art. CT images, including helical, volumetric CT images, may thereby be generated based on the reconstruction algorithms and Weighting Functions W(n) discussed above. The radiation beam 326 may be a fan beam, in which case the detector array 301 would be one dimensional, comprising a single row of detector modules and gaps, arranged in a circle. The radiation beam 326 may also be a cone beam, in which case the detector array 301 would be two dimensional, comprising rows and columns of detector modules arranged in a circle. In the two dimensional case, in the projection of the mirror image of the pie-shaped regions, detector modules in the pie-shaped region would overlap gaps in the other pie-shaped region, and vice-a-versa, in both dimensions, as discussed above with respect to FIG. 12.

The collimator 325 may comprise a plurality of sections that are movable perpendicular to the plane of the circle around which the source 324 is moved, similar to collimators used in fourth generation CT systems to reduce scatter. The plurality of sections may be automatically moved in front of the source as the source moves around the object to selectively allow radiation to be directed toward the object and received by the detector elements 4 of each detector modules, and block the radiation that would impact the detector electronics sections 5, 6, 7 in the gaps. (See FIG. 1). A stationary collimator may be provided in front of the detector array with openings to allow the passage of radiation to the detector elements of each module but not to the housing of each module or to the gaps, as discussed above, instead of or along with the collimator in front of the source.

Figure 16:
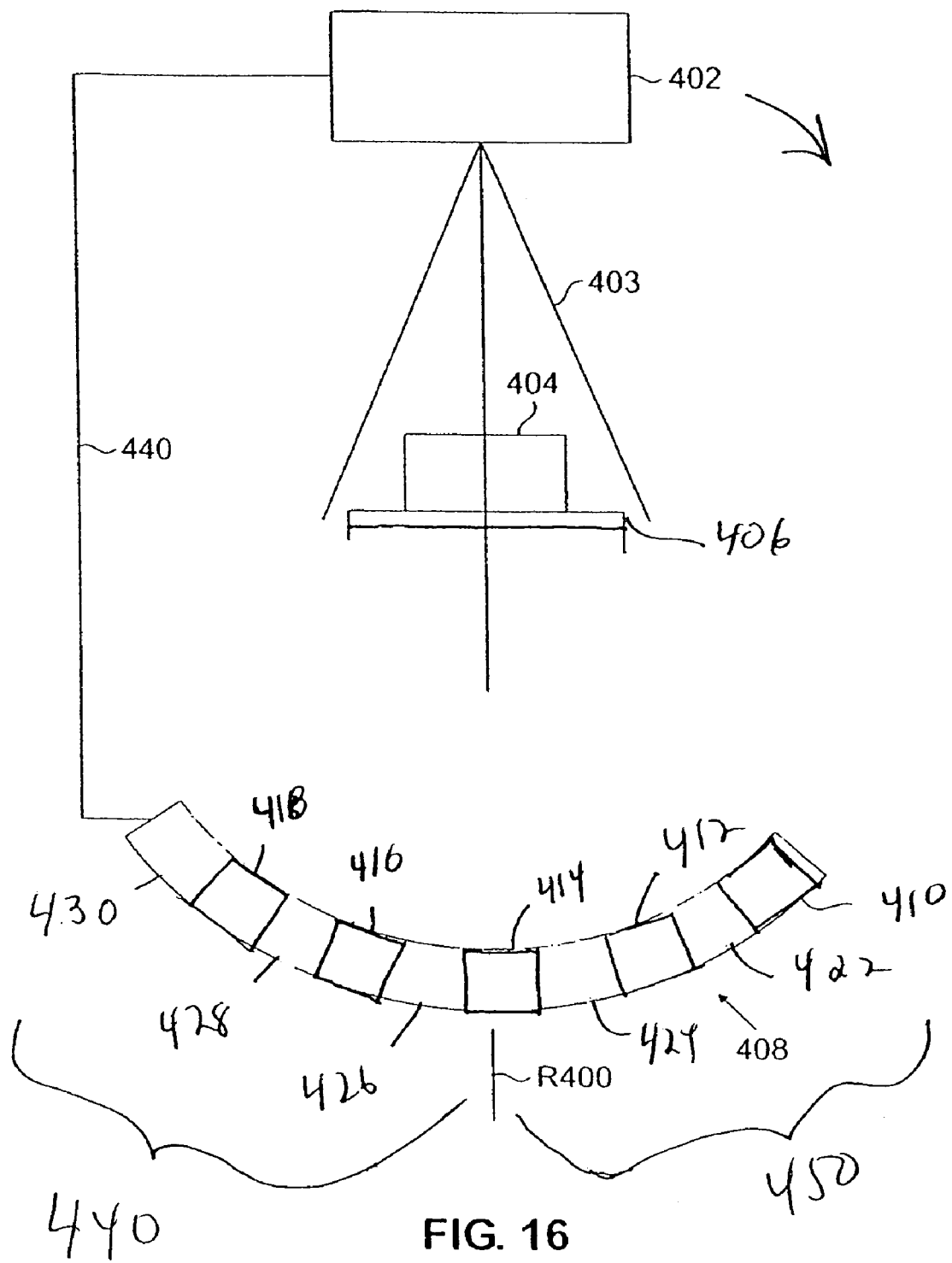
FIG. 16 is a schematic representation of a front view of a third generation scanning unit in accordance with an embodiment of the invention.

Gaps may also be provided in a detector array used in a third generation CT system. FIG. 16 is a schematic representation of a front view of a third generation CT system 400 showing a source 402 emitting a beam 403 and an object 404 supported on a support 406. A detector array 408 comprises modules 410, 412, 414, 416, 418 separated by gaps 422, 424, 426, 428. The detector array 408 is arranged in a similar manner as the detector array 19 in FIG. 9. No detector module need be provided at one end 430 of the detector array 408. The source 402 and the detector array 408 are supported by a gantry 440, which rotates the source and the detector around the object 404. The gantry 440 moves the source 402 and the detector 408 together, in this example clockwise, so that they are stationary with respect to each other. Also in this example, the support 406 moves the object along an axis out of the page, and through the beam 403, continuously or incrementally. A ray R400 is shown extending from the source 402 through the detector array 408. A projection of a mirror image of the detectors 416 and 418 on one side 440 of the ray R400 at least fill the gaps 422, 424 on the other side 450 of the ray, as in the embodiment of FIG. 9. Preferably, portions of the detector modules 416, 418 overlap portions of the modules 410, 412, 414 in the projection, as above. Collimation of the radiation beam 403 at the source 402 and/or at the detector array 408 may be provided, as is also discussed above. CT images, including helical, volumetric CT images, may thereby be generated based on the reconstruction algorithms and Weighting Functions W(n) discussed above.

While the object discussed above is often referred to as a cargo conveyance or cargo container, the object may also be another type of object, such as luggage and bags. In addition, the object may be a person and medical CT may be performed.

The present invention may also be used in conjunction with other radiation inspection techniques known in the art, such as detecting scattered radiation, prescanning, use of pencil beams, laminar tomography, conventional planar tomography, inducing fission of fissionable material and detection of stimulated emissions, such as NRF, for example, as described in the '060 Application, which is incorporated by reference, herein. Additional sources and detectors may be provided to conduct any of these other tests, if desired or needed, or the same source(s)/detector(s) described and illustrated herein may be used.

One skilled in the art will recognize that other changes may be made to the embodiments described herein without departing from the spirit and scope of the invention, which is defined by the claims, below.

What is claimed is:

1. A scanning unit for inspecting cargo conveyances, the scanning unit comprising:
    a radiation source to emit a beam of radiation;
    a rotatable platform configured to support a cargo conveyance for inspection by the beam of radiation, the rotatable platform being rotatable about an axis; and
    a detector positioned to collect at least certain of the radiation transmitted through the cargo conveyance, the detector comprising a plurality of modules separated by at least one gap;
    wherein:
    at least one of the platform, the source, or the detector is movable along a direction of the axis; and
    the plurality of detector modules are positioned with respect to a ray from the source through a center of rotation of the object during rotation by the platform such that a mirror image of first detector modules on one side of the ray, projected onto the other side of the ray, at least coincides with the at least one gap between second detector modules on the other side of the array, to collect a sufficient data set of radiation to reconstruct computed tomographic images.

2. The radiation scanning system of claim 1, wherein:
    the projection of the mirror image of the first detector modules coincides with the at least one gap and overlaps portions of the second modules; and
    the system further comprises a processor configured to:
    apply at least one first weighting value to data collected by overlapping portions of the detector modules; and
    apply at least one second weighting value to data collected from detector elements in non-overlapping portions of the detector modules;
    wherein the first weighting value is less than the second weighting value.

3. The scanning unit of claim 1, further comprising a processor coupled to the detector to reconstruct computed tomography images from data received from the detector.

4. The scanning unit of claim 1, wherein:
    the beam is a cone beam or a fan beam.

5. The scanning unit of claim 4, wherein:
    the beam is a cone beam and the detector comprises a detector array comprising a plurality of two dimensional detectors.

6. The scanning unit of claim 1, wherein:
    the source and the detector are stationary; and
    the platform is movable along the axis.

7. A scanning unit for inspecting objects, the scanning unit comprising:
a radiation source to emit a beam of radiation;
a rotatable platform to support an object for inspection by the beam of radiation, the rotatable platform being rotatable about an axis; and
a detector array positioned to receive radiation transmitted through the object, the detector array comprising a first plurality of modules separated by a second plurality of gaps;
wherein:
the plurality of modules are positioned with respect to a ray from the source through a center of rotation of the object during rotation by the platform such that a mirror image of first detector modules on one side of the ray, projected onto the other side of the ray, at least coincides with the gaps between second detector modules on the other side of the array; and
at least one of the radiation source, the platform and or the detector is movable along a direction of the axis.

8. The scanning unit of claim 7, wherein:
the radiation beam is a fan beam.

9. The scanning unit of claim 7, wherein:
the radiation beam is a cone beam; and
the detector array comprises a plurality of rows and columns of detector modules separated by respective first gaps between detector modules in adjacent rows and by respective second gaps between detector modules in adjacent columns;
wherein:
the rows of detector modules are positioned so that a first projection of the detector modules on one side of a first axis perpendicular to the first ray and perpendicular to a direction of the rows, onto the other side of the first axis, at least coincides with the plurality of gaps on the other side; and
the columns are positioned so that a projection of the detector modules on one side of a second axis perpendicular to the first ray and perpendicular to a direction of the columns onto the other side of the axis at least coincides with the plurality of gaps on the other side.

10. The scanning unit of claim 7, wherein:
the source and the detector are stationary; and
the platform is movable along the axis.

11. The scanning unit of claim 7, further comprising:
a processor programmed to reconstruct computed tomographic images based, at least in part, on radiation collected by the detector array.

12. The radiation scanning system of claim 7, wherein:
the projection of the mirror image of the first detector modules coincides with the gaps and overlaps portions of the second modules; and
the processor is configured to:
apply at least one first weighting value to data collected by overlapping portions of the detector modules; and
apply at least one second weighting value to data collected from detector elements in non-overlapping portions of the detector modules;
wherein the first weighting value is less than the second weighting value.

13. The scanning unit of claim 7, wherein:
each of the plurality of modules comprises detector elements and at least one electronics section; and
the scanning unit further comprises a collimator coupled to the source, the collimator defining a plurality of openings, at least some of the openings corresponding to respective modules of the detector array;
the openings being configured to allow passage of radiation to irradiate the detector elements of a respective module and not to allow passage of radiation to irradiate the at least one electronics section of the module.

14. A radiation scanning system comprising:
a radiation source;
a detector comprising an expanse of detector modules and defining at least one gap between adjacent detector modules along the expanse;
a movable platform to support the object; and
a processor to reconstruct computed tomographic images based, at least in part, on data provided by the detector;
wherein:
the at least one gap is positioned such that at least some line integrals through the object are measured only once.

15. The radiation scanning system of claim 13, wherein:
the at least one gap is positioned such that a mirror image of the expanse of first detector modules on one side of a ray from the source through the object, projected onto the other side of the ray, at least coincides with the at least one gap between second detector modules on the other side of the ray.

16. The radiation scanning system of claim 15, wherein:
in the projection, the first detector modules overlap respective portions of the second modules; and
the processor is configured to:
apply at least one first weighting value to data collected by overlapping portions of the detector modules; and
apply at least one second weighting value to data collected from detector elements in non-overlapping portions of the detector modules;
wherein the first weighting value is less than the second weighting value.

17. The scanning unit of claim 14, wherein:
the radiation source is movable around the object;
the detector array is movable with movement of the source; and
the detector array extends only partially around the object.

18. The scanning unit of claim 14, wherein:
the radiation source is movable around the object;
the detector array is stationary; and
the detector array extends completely around the object.

19. The radiation scanning system of claim 14, wherein the processor is further programmed to:
reconstruct the computed tomographic images by weighting the collected data.

20. The radiation scanning system of claim 14, wherein:
a plurality of gaps are defined by spaces between selected adjacent detector modules.

21. A method of examining contents of a cargo conveyance, comprising:
rotating the cargo conveyance about an axis of rotation;
moving at least one of the cargo conveyance, a source of a beam of radiation, or a detector along the axis;
scanning the cargo conveyance with a radiation beam; and
measuring at least some line integrals though the cargo conveyance only once by:
detecting radiation in at least one first location on one side of the ray passing through the object and not in at least one second other location;
detecting radiation in at least one third location on the other side of a ray and not in at least one fourth location;
wherein:
in a projection of a mirror image of the one side of the ray onto the other side of the ray, the at least one first location on the one side at least coincides with the at least one fourth location on the other side;

the method further comprising reconstructing computed tomographic images based on the detected radiation.

22. The method of claim 21, further comprising:
rotating the cargo conveyance about an axis; and
moving at least one of the cargo conveyance, the source and the detector in a direction of the axis.

23. The method of claim 21, further comprising:
moving at least one of the source and the detector around the object; and
moving the cargo conveyance through the radiation beam.

24. A method of examining contents of an object, comprising:
scanning the object with a radiation beam from a source;
detecting radiation in at least one first location on one side of the ray passing through the object and not in at least one second other location;
detecting radiation in at least one third location on the other side of a ray and not in at least one fourth location;
wherein:
in a projection of a mirror image of the one side of the ray onto the other side of the ray, the at least one first location on the one side at least coincides with the at least one fourth location on the other side.

25. The method of claim 24, comprising:
detecting radiation interacting with the object by a first plurality of detector modules separated by at least one gap.

26. The method of claim 24, wherein:
in the projection, the at least one first location coincides with the at least one fourth location and overlaps a portion of the at least one third location.

27. The method of claim 24, wherein the at least one first location comprises a plurality of detector modules and the at least one third location comprises a plurality of detector modules, the method comprising reconstructing tomographic images by:
applying at least one first weighting value to data collected by overlapping portions of the detector modules; and
applying at least one second weighting value to data collected by non-overlapping portions of the detector modules;
wherein the at least one first weighting value is less than the at least one second weighting value.

28. The method of claim 24, comprising:
moving the source around the object while scanning.

29. The method of claim 28, comprising:
detecting the radiation by a stationary detector array extending around the object.

30. The method of claim 28, wherein the detector array extends partially around the source, the method comprising:
moving the detector array with movement of the source; and
detecting the radiation by the moving detector array.

31. A scanning unit for inspecting cargo conveyances, the scanning unit comprising:
a radiation source to emit a beam of radiation;
a rotatable platform configured to support a cargo conveyance for inspection by the beam of radiation;
a collimator configured to collimate the beam of radiation such that the beam of radiation has a first boundary extending beyond an edge of the cargo conveyance and a second boundary intercepting the cargo conveyance during rotation of the cargo conveyance;
a detector positioned to collect at least certain of the radiation transmitted through the cargo conveyance;

a processor coupled to the detector, the processor configured to reconstruct computed tomographic images based, at least in part, on the radiation detected by the detector;
wherein:
at least one of the platform, the source, and or the detector is movable along a direction of the axis; and
the detector is configured to collect a sufficient data set of radiation to reconstruct computed tomographic images.

32. The system of claim 31, wherein the processor is configured to:
apply at least one first weighting value to line integrals collected by the detector once; and
apply at least one second weighting factor to line integrals collected by the detector more than once, the second weighting factor being smaller than the first weighting factor.

33. The scanning unit of claim 31, wherein:
the source and the detector are stationary; and
the platform is movable along the axis.

34. The system of claim 31, wherein the processor is configured to:
apply at least one first weighting value to line integrals collected by the detector once; and
apply at least one second weighting factor to line integrals collected by the detector more than once, the second weighting factor being smaller than the first weighting factor.

35. A method of inspecting cargo conveyances, comprising:
rotating a cargo conveyance about an axis;
collimating a radiation beam to have a first boundary extending beyond an edge of the cargo conveyance and a second boundary intercepting the cargo conveyance during rotation of the cargo conveyance;
moving at least one of the cargo conveyance, the source or the detector along a direction of the axis;
detecting at least certain of the radiation detected by the detector; and
reconstructing computed tomographic images from the detected radiation.

36. The method of claim 35, further comprising:
applying at least one first weighting value to line integrals collected by the detector once; and
applying at least one second weighting factor to line integrals collected by the detector more than once, the second weighting factor being smaller than the first weighting factor.

37. The method of claim 35, further comprising:
moving the rotating platform along the axis.

38. A scanning unit for inspecting cargo conveyances, the scanning unit comprising:
an X-ray radiation source to emit a beam of radiation;
a rotatable platform configured to support a cargo conveyance for inspection by the beam of radiation, the platform being rotatable about an axis and movable along a direction of the axis, in steps;
a collimator configured to collimate the beam of radiation such that the beam of radiation has a first boundary extending beyond an edge of the cargo conveyance and a second boundary intercepting the cargo conveyance during rotation of the cargo conveyance;
a detector positioned to collect a sufficient data set of radiation transmitted through the cargo conveyance to reconstruct computed tomographic images; and a processor coupled to the detector, the processor configured to reconstruct computed tomographic images based, at least in part, on the radiation detected by the detector.

39. A method of inspecting cargo conveyances, comprising:
rotating a cargo conveyance about an axis;
collimating a radiation beam to have a first boundary extending beyond an edge of the cargo conveyance and a second boundary intercepting the cargo conveyance during rotation of the cargo conveyance;
moving the cargo conveyance along a direction of the axis, in steps;
detecting at least certain of the radiation detected by the detector; and
reconstructing computed tomographic images from the detected radiation.

40. The method of claim 39, further comprising:
applying at least one first weighting value to line integrals collected by the detector once; and
applying at least one second weighting factor to line integrals collected by the detector more than once, the second weighting factor being smaller than the first weighting factor.

* * * * *